(12) United States Patent
Daoud et al.

(10) Patent No.: US 12,016,567 B2
(45) Date of Patent: *Jun. 25, 2024

(54) SYSTEMS AND METHODS FOR MECHANICAL DISPLACEMENT OF AN ESOPHAGUS

(71) Applicants: Ohio State Innovation Foundation, Columbus, OH (US); S4 Medical Corp, Chagrin Falls, OH (US)

(72) Inventors: Emile Daoud, Chagrin Falls, OH (US); William Fuller, Chagrin Falls, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 244 days.

This patent is subject to a terminal disclaimer.

(21) Appl. No.: 17/859,694

(22) Filed: Jul. 7, 2022

(65) Prior Publication Data

US 2022/0346799 A1 Nov. 3, 2022

Related U.S. Application Data

(62) Division of application No. 16/847,958, filed on Apr. 14, 2020, now Pat. No. 11,382,631.

(51) Int. Cl.
*A61B 17/12* (2006.01)
*A61B 17/00* (2006.01)
(Continued)

(52) U.S. Cl.
CPC .. *A61B 17/12104* (2013.01); *A61B 17/00234* (2013.01); *A61B 17/0218* (2013.01);
(Continued)

(58) Field of Classification Search
CPC ........ A61B 17/12104; A61B 17/00234; A61B 17/0218; A61B 17/12136; A61B 17/3431;
(Continued)

(56) References Cited

U.S. PATENT DOCUMENTS

2007/0010782 A1 1/2007 Doty et al.
2007/0215162 A1 9/2007 Glassenberg et al.
(Continued)

OTHER PUBLICATIONS

International Search Report and Written Opinion issued for Application No. PCT/US2021/027113, dated Aug. 2, 2021, 11 pages.
(Continued)

*Primary Examiner* — Kelly J Bekker
*Assistant Examiner* — Andrew P. Restaino
(74) *Attorney, Agent, or Firm* — Meunier Carlin & Curfman LLC

(57) ABSTRACT

Assembly for use with a vacuum system and an esophageal positioning device esophageal positioning device includes an introducer, in which the esophageal positioning device includes a first segment and a second segment. The second segment is pivotally connected to the first segment. A gap portion of an outer tube of the introducer is defined along a longitudinal axis between a tube tip of the introducer and the distal end of the second segment of the esophageal positioning device when the esophageal positioning device is disposed within the introducer. The gap portion defines one or more radial vacuum holes.

10 Claims, 38 Drawing Sheets

(51) Int. Cl.
A61B 17/02 (2006.01)
A61B 17/34 (2006.01)
A61B 34/00 (2016.01)
A61B 90/00 (2016.01)

(52) U.S. Cl.
CPC .... *A61B 17/12136* (2013.01); *A61B 17/3431* (2013.01); *A61B 34/70* (2016.02); *A61B 2017/00243* (2013.01); *A61B 2017/00292* (2013.01); *A61B 2017/003* (2013.01); *A61B 2017/00336* (2013.01); *A61B 2017/345* (2013.01); *A61B 2017/348* (2013.01); *A61B 2017/3488* (2013.01); *A61B 2090/0427* (2016.02); *A61B 2217/005* (2013.01)

(58) Field of Classification Search
CPC .......... A61B 34/70; A61B 2017/00243; A61B 2017/00292; A61B 2017/003; A61B 2017/00336; A61B 2017/345; A61B 2017/348; A61B 2017/3488; A61B 2090/0427; A61B 2217/005; A61B 2017/306; A61B 2018/00291; A61B 17/12045; A61B 17/12099; A61B 90/04; A61B 2017/00818; A61M 1/0058; A61M 1/85; A61M 16/043
See application file for complete search history.

(56) References Cited

U.S. PATENT DOCUMENTS

| | | |
|---|---|---|
| 2008/0033415 A1 | 2/2008 | Rieker et al. |
| 2014/0188080 A1 | 7/2014 | Besser et al. |
| 2017/0252027 A1 | 9/2017 | Kasic |
| 2017/0360503 A1 | 12/2017 | Miller |
| 2018/0317943 A1 | 11/2018 | Razavi et al. |
| 2019/0223734 A1 | 7/2019 | Lakkireddy et al. |
| 2019/0269834 A1 | 9/2019 | Oza et al. |

OTHER PUBLICATIONS

Arbelo E, Brugada J, Lundqvist CB, Laroche C, Kautzner J, Pokushalov E, Raatikainen P, Efremidis M, Hindricks G, Barrera A, Maggioni A, Tavazzi L, Dagres N. Contemporary management of patients undergoing atrial fibrillation ablation: in-hospital and 1-year follow-up findings from the ESC-EHRA atrial fibrillation ablation long-term registry. Eur Heart J. 2017;38:1302-1316.
Aryana A, Arthur A, O'Neill PG, D'Avila A. Catastrophic manifestations of air embolism in a patient with atrio-esophageal fistula following minimally invasive surgical ablation of atrial fibrillation. J Cardiovasc Electrophysiol 2013;24:933-934.
Bhardwaj R,Naniwadekar A, Whang W, Mittnacht AJ, Palaniswamy C, Koruth JS, Joshi K, Sofi A, Miller M, Choudry S, Dukkipati SR, Reddy VY: Esophageal deviation during atrial fibrillation ablation J Am Coll Cardiol EP 2018;4:1020-30.
Black-Maier E, Pokorney SD, Barnett AS, Zeitler EP, Sun AY, Jackson KP, Bahnson TD, Daubert JP, Piccini JP: Risk of atrioesophageal fistula formation with contact force-sensing catheters. Heart Rhythm 2017;14:1328-1333.
Borchert B, Lawrenz T, Hansky B, Stellbrink C. Lethal atrio-esophageal fistula after pulmonary vein isolation using high-intensity focused ultrasound (HIFU). Heart Rhythm 2008;5:145-148.
Cappato R, Calkins H, Chen SA, Davies W, Iesaka Y, Kalman J, Kim YH, Klein G, Natale A, Packer D, Skanes A, Ambrogi F, Biganzoli E. Updated worldwide survey on the methods, efficacy, and safety of catheter ablation for human atrial fibrillation. Circ Arrhythm Electrophysiol. 2010;3:32-38.
Cummings JE, Schweikert RA, Saliba WI, Burkhardt JD, Brachmann J, Gunther J,Schibgilla V, Verma A, Dery M, Drago JL, Kilicaslan F, Natale A. Assessment of temperature, proximity, and course of the esophagus during radiofrequency ablation within the left atrium. Circulation 2005;112(4):459-64.
Cummings JE, Schweikert RA, Saliba WI, et al. Brief communication: atrial-esophageal fistulas after radiofrequency ablation. Ann Intern Med 2006; 144: 572-574.
Giacomino BD, Worden N, Marchigiani R, Keech J, Giudici MC. Pericardial-esophageal fistula complicating cryoballoon ablation for refractory atrial fibrillation. Heart Rhythm Case Rep. 2017, 5 pages.
Halbfass P, Müller P, Nentwich K, Krug J, Roos M, Hamm K, Barth S, Szöllösi A,Mügge A, Schieffer B, Deneke T. Incidence of asymptomatic oesophageal lesions after atrial fibrillation ablation using an oesophageal temperature probe with insulated thermocouples: a comparative controlled study. Europace. 2016;19:385-391.
Halbfass P, Pavlov B, Müller P, Nentwich K, Sonne K, Barth S, Hamm K, Fochler F, Mügge A, Lüsebrink U, Kuhn R, Deneke T. Progression From esophageal thermal asymptomatic Lesion to perforation complicating atrial fibrillation ablation: a single-center registry. Circ Arrhythm Electrophysiol. Aug. 2017;10(8), 10 pages.
Herweg B, Johnson N, Postler G, Curtis AB, Barold SS, Ilercil A. Mechanical esophageal deflection during ablation of atrial fibrillation. Pacing Clin Electrophysiol. 2006;29(9):957-61.
Knopp H, Halm U, Lamberts R, Knigge I, Zachäus M, Sommer P, Richter, S,Bollmann A, Hindricks G, Husser D. Incidental and ablation-induced findings during upper gastrointestinal endoscopy in patients after ablation of atrial fibrillation: a retrospective study of 425 patients. Heart Rhythm. 2014;11:574-578.
Kuck KH, Brugada J, Fürnkranz A, Metzner A, Ouyang F, Chun KR, Elvan A, Arentz T, Bestehorn K, Pocock SJ, Albenque JP, Tondo C; Fire and Ice Investigators. Cryoballoon or Radiofrequency Ablation for Paroxysmal Atrial Fibrillation. N Engl J Med. Jun. 9, 2016;374(23):2235-45.
Mateos JC, Mateos EI, Peña TG, Lobo TJ, Mateos JC, Vargas RN, Pachón CT,Acosta JC. Simplified method for esophagus protection during radiofrequency catheter ablation of atrial fibrillation—prospective study of 704 cases. Rev Bras Cir Cardiovasc. 2015;30(2):139-47.
Metzner A, Burchard A, Wohlmuth P, Rausch P, Bardyszewski A, Gienapp C, Tilz RR, Rillig A, Mathew S, Deiss S, Makimoto H, Ouyang F, Kuck KH, Wissner E. Increased incidence of esophageal thermal lesions using the second-generation 28-mm cryoballoon. Circ Arrhythm Electrophysiol. 2013;6(4):769-75.
Müller P, Dietrich JW, Halbfass P, Abouarab A, Fochler F, Szöllösi A, Nentwich K, Roos M, Krug J, Schade A, Mügge A, Deneke T. Higher incidence of esophageallesions after ablation of atrial fibrillation related to the use of esophageal temperature probes. Heart Rhythm. 2015;12:1464-1469.
Nakagawa H, Seres KA, Jackman WM. Limitations of esophageal temperature monitoring to prevent esophageal injury during atrial fibrillation ablation. Circ Arrhythm Electrophysiol. 2008;1(3):150-2.
Palaniswamy C, Koruth JS, Mittnacht AJ, Miller MA, Choudry S, Bhardwaj R, Sharma D, Willner JM, Balulad SS, Verghese E, Syros G, Singh A, Dukkipati SR, Reddy VY: The extent of mechanical esophageal deviation to avoid esophageal heating during catheter ablation of atrial fibrillation. J Am Coll Cardiol EP 2017;3:1146-54.
Pappone C, Oral H, Santinelli V, et al. Atrio-esophageal fistula as a complication of percutaneous transcatheter ablation of atrial fibrillation. Circulation 2004;109:2724-2726.
Parikh V, Swarup V, Hantla J, Vuddanda V, Dar T, Yarlagadda B, Biase LD, Al-Ahmad A, Natale A, Lakkireddy D: Feasibility, safety and efficacy of a novel preshaped nitinol esophageal deviator to successfully deflect the esophagus and ablate left atrium without esophageal temperature rise during atrial fibrillation ablation—The Deflect Gut study. Heart Rhythm. 2018; 15(9):1321-1327.
Rillig A, Meyerfeldt U, Birkemeyer R, Wiest S, Sauer BM, Staritz M, Jung W.Oesophageal temperature monitoring and incidence of oesophageal lesions after pulmonary vein isolation using a remote robotic navigation system. Europace 2010;12:655-661.

(56) References Cited

OTHER PUBLICATIONS

Sánchez-Quintana D, Cabrera JA, Climent V, Farré J, Mendonça MC, Ho SY. Anatomic relations between the esophagus and left atrium and relevance for ablation of atrial fibrillation. Circulation. 2005;112(10):1400-5.

Schmidt M, Nölker G, Marschang H, Gutleben KJ, Schibgilla V, Rittger H, Sinha AM, Ritscher G, Mayer D, Brachmann J, Marrouche NF: Incidence of oesophageal wall injury post-pulmonary vein antrum isolation for treatment of patients with atrial fibrillation. Europace 2008;10:205-9.

Sohara H, Satake S, Takeda H, Yamaguchi Y, Nagasu N. Prevalence of esophageal ulceration after atrial fibrillation ablation with the hot balloon ablation catheter: what is the value of esophageal cooling? J Cardiovasc Electrophysiol.2014;25:686- 92.

Sommer P, Hindricks G. Prevention of oesophageal injury during catheter ablation of atrial fibrillation: is monitoring of oesophageal temperature the solution? Europace. 2010;12(7):911-2.

Stockigt F, Schrickel JW, Andrie R, Lickfett L. Atrio-esophageal fistula after cryoballoon pulmonary vein isolation. J Cardiovasc Electrophysiol 2012;12:1254-1257.

European Patent Office. Extended European Search Report. Issued in EP Application No. 21789123.3. Apr. 15, 2024. 12 pages.

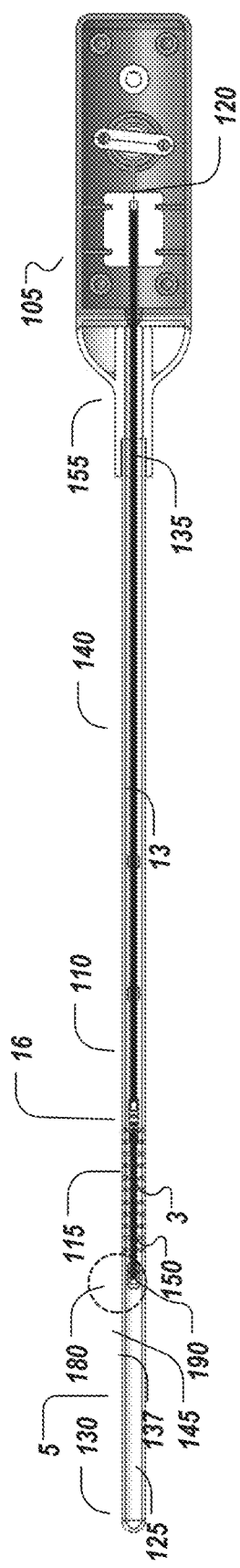
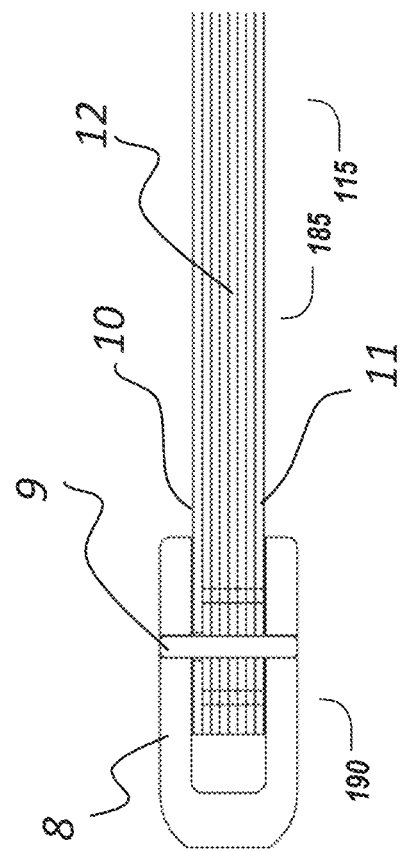
FIG. 5
FIG. 6

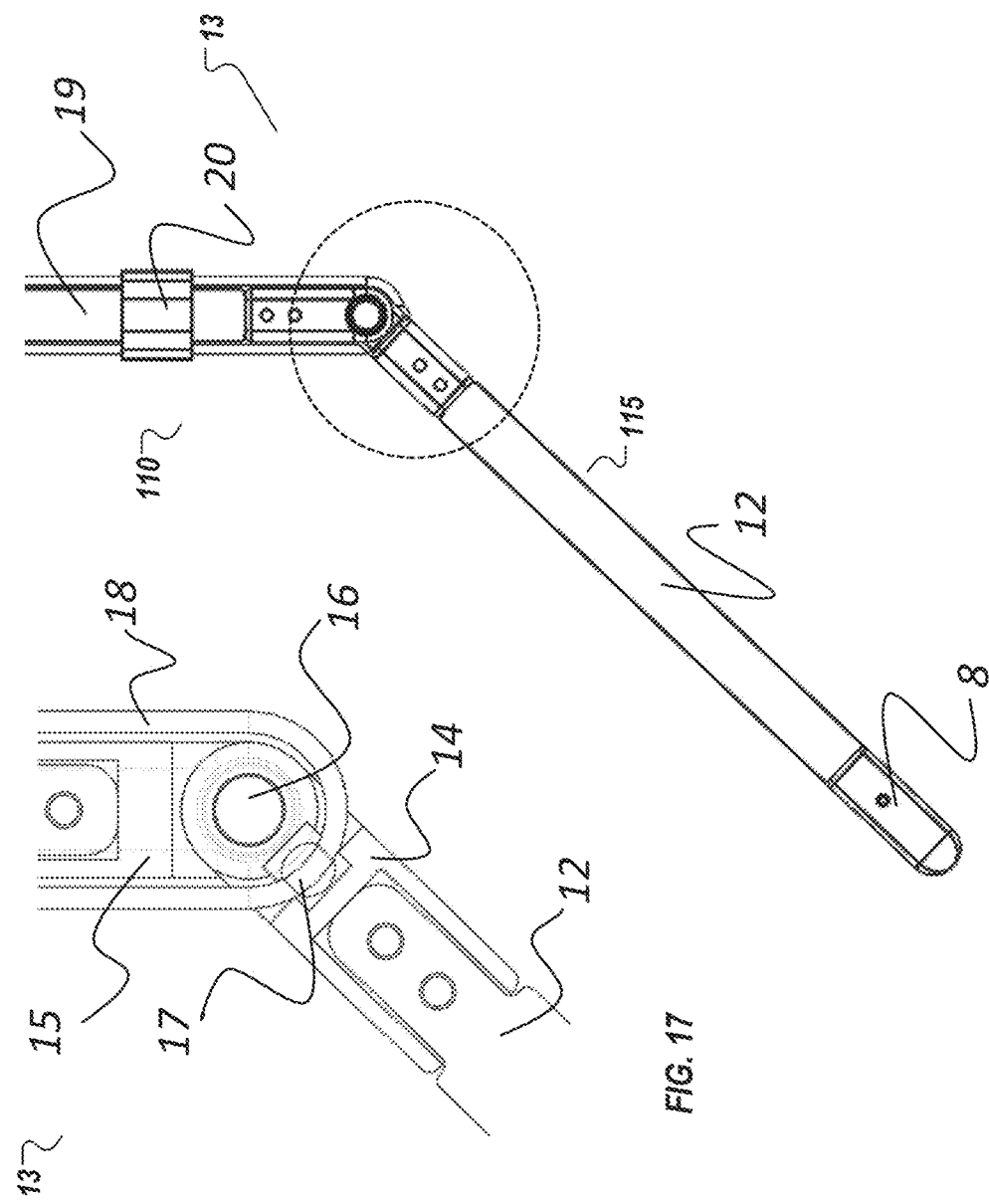

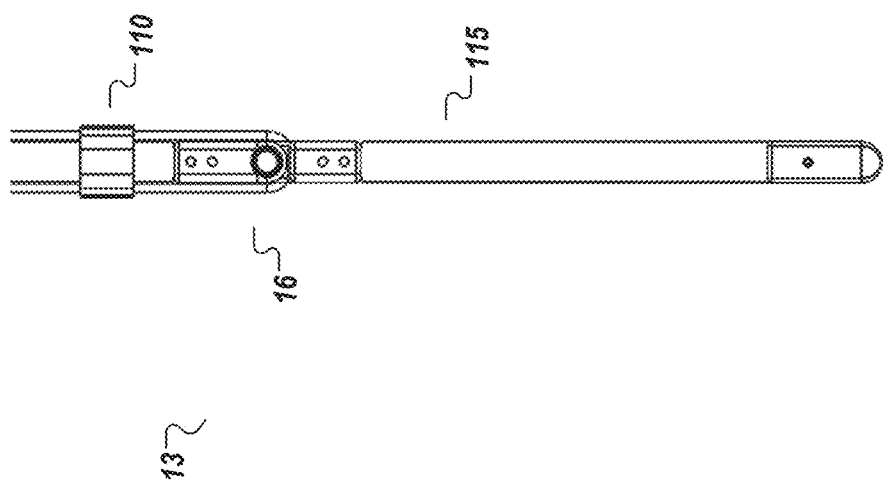

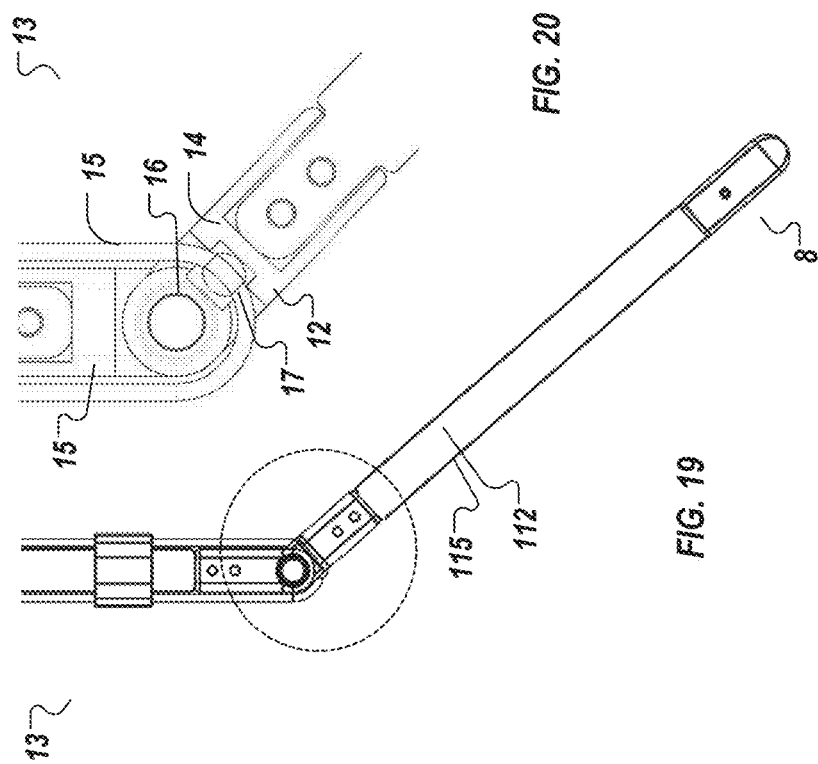

SYSTEMS AND METHODS FOR MECHANICAL DISPLACEMENT OF AN ESOPHAGUS

CROSS REFERENCE TO RELATED APPLICATIONS

This application is a division of U.S. application Ser. No. 16/847,958, filed Apr. 14, 2020, the content of which is herein incorporated by reference in its entirety.

TECHNICAL FIELD

This disclosure relates to medical devices and methods for vacuum suction adherence of the esophagus coupled with mechanical displacement of an esophagus of a patient.

BACKGROUND

It has been projected that, the number of patients experiencing atrial fibrillation ("AF") will increase to 10 million in 20 years. The cost of treating a patient with AF ranges from $2,000 U.S. to over $10,000 U.S. each year. The most effective and expanding method of treating AF is with a procedure called catheter ablation. Catheter ablation is designed to deliver energy (for example, radiofrequency and cryoenergy) through a catheter that is placed in the left atrium of the heart. The ablation results in destruction of the heart cells. The areas of the heart that are targeted for ablation are the areas that cause AF. These areas in the left atrium lie within 2-4 millimeters of the esophagus, thus a major concern is that energy from the ablation catheter can radiate forward and injure the esophagus. In the United States, approximately 103,000 AF ablation procedures are performed each year, and an additional 57,000 procedures are performed outside the U.S. A serious complication of an AF ablation procedure is injury to the esophagus that results in an atrial-esophageal fistula. This communication between the esophagus and the heart occurs because the ablation energy inflames the heart and the esophagus. The subsequent healing results in a hole/communication between the heart (a sterile organ) and the esophagus (not sterile organ). This communication may result in an infection of the heart and stroke. An atrial-esophageal fistula occurs in about 0.6% of patients and the outcome is nearly always fatal or associated with significant morbidity. Furthermore, the precursor to an atrial-esophageal fistula is ulcers in the esophagus, which are also due to injury of the esophagus and occurs in about 30% of patients. Hence electrophysiologists, physicians who perform the ablation procedure, are quite concerned about preventing damage to the esophagus and to avoid atrial-esophageal fistula.

Conventional therapy includes inserting a device into the esophagus to monitor temperature and to abort delivery of ablation energy once there is a change in luminal esophageal temperature. However, these devices are unable to displace the esophagus away from the energy source of the ablation and thus do not offer an active protective mechanism to guard against injury to the esophagus.

Therefore, improved systems for displacing an esophagus are needed so to reduce the risk of injury to the esophagus.

SUMMARY

Provided are devices, systems, and methods for vacuum suction adherence and mechanical displacement of an esophagus. In particular, disclosed are assemblies for use with a vacuum system and an esophageal positioning device. Disclosed as well are mechanical esophageal displacement systems, and methods of use.

The esophagus is a flexible muscular organ and is often moved during medical procedures. If mere mechanical force is applied to move the esophagus, tenting of the esophagus may result rather than actual movement and displacement of a region of the organ. More specifically, the mechanical force will displace the leading edge of the esophageal wall, but the trailing edge of the esophageal wall will move only a small distance, if any. The resulting tenting of the esophagus fails to provide protective benefit from the mechanical displacement. The systems disclose herein utilize suction vacuum to apply a uniform force to the esophagus to pull the esophageal wall in and adhere the esophageal walls in a circumferential manner. Under this physiologic condition, along with application of a mechanical force, the entire circumferential segment of the esophagus is displaced and there is no lagging or trailing edge of the esophagus. In general, the esophagus follows the directional changes of the esophageal positioning device via the assembly. This directional change can be easily visualized by the physician on the x-ray equipment via the use of radiopaque markers. The visualization provides immediate feedback to the physician. By moving the esophagus outside the ablation field, the AF procedure can proceed relatively safely without risk of damage to the esophagus, and the operator can ablate the targeted areas with confidence without concern for esophageal damage.

An example assembly includes an introducer for use with a vacuum system and an esophageal positioning device esophageal positioning device. The esophageal positioning device includes a handle, a first segment, a second segment, and an articulation driving mechanism. The first segment being coupled to the handle. The second segment being pivotally connected to the first segment. The articulation driving mechanism being configured to pivot the second segment about the first segment upon articulation. In some embodiments, the second segment is sized to displace the esophageal wall by about 4 centimeters upon articulation.

The introducer of the example assembly includes a soft cyclical outer tube, and a tube tip. The soft outer tube being sized to pass through a mouth or nasal passage into an esophagus, in which the soft outer tube includes a distal end, a proximal end, a lumen, and a body. The body of the outer tube includes a perforated outer surface, and one or more internal vacuum passages that extend a distance from the proximal end towards the distal end within the body of the outer tube. In some embodiments, the perforated outer surface includes a plurality of vacuum holes spaced circumferentially around, and extending radially from, the soft outer tube. Because the plurality of vacuum holes are spaced circumferentially around the soft outer tube, the plurality of vacuum holes are located on multiple sides of the tube and can suction the esophagus from multiple directions. The one or more internal vacuum passages are in fluid communication with the plurality of vacuum holes to apply a vacuum to an esophageal wall via the vacuum system. The tube tip is located at the distal end of the outer tube.

An example mechanical esophageal displacement system includes an assembly and an esophageal positioning device, in which the assembly is operatively coupleable to a vacuum system. The assembly comprises an introducer that includes a soft cyclical outer tube, and a tube tip. The soft outer tube being sized to pass through a mouth or nasal passage into an esophagus, in which the soft outer tube includes a distal end, a proximal end, a lumen, and a body. The body of the outer tube includes a perforated outer surface and one or more internal vacuum passages that extend a distance from the proximal end towards the distal end within the body of the outer tube. In some embodiments, the perforated outer surface includes a plurality of vacuum holes spaced circumferentially around, and extending radially from, the soft outer tube. Because the plurality of vacuum holes are spaced circumferentially around the soft outer tube, the plurality of vacuum holes are located on multiple sides of the tube and can suction the esophagus from multiple directions. The one or more internal vacuum passages are in fluid communication with the plurality of vacuum holes to apply a vacuum to an esophageal wall via the vacuum system. The tube tip being located at the distal end of the outer tube.

The esophageal positioning device of the example mechanical esophageal displacement system includes a handle, a first segment, a second segment, and an articulation driving mechanism. The first segment being coupled to the handle. The second segment being pivotally connected to the first segment. The articulation driving mechanism being configured to pivot the second segment about the first segment upon articulation.

An example method of using a mechanical esophageal displacement system includes inserting an assembly into an esophagus of a patient via a mouth or nasal passage. The assembly includes an introducer having a soft cyclical outer tube, a vacuum port, and a tube tip. The soft outer tube being sized to pass through a mouth or nasal passage into an esophagus, in which the soft outer tube includes a distal end, a proximal end, a lumen, and a body. The body of the outer tube includes a perforated outer surface and one or more internal vacuum passages that extend a distance from the proximal end towards the distal end within the body of the outer tube. In some embodiments, the perforated outer surface includes a plurality of vacuum holes spaced circumferentially around, and extending radially from, the soft outer tube. Because the plurality of vacuum holes are spaced circumferentially around the soft outer tube, the plurality of vacuum holes are located on multiple sides of the tube and can suction the esophagus from multiple directions. The one or more internal vacuum passages are in fluid communication with the plurality of vacuum holes to apply a vacuum to an esophageal wall via the vacuum system. The tube tip being located at the distal end of the outer tube. The vacuum port includes a vacuum port body, a vacuum line hook up, and a vacuum port cap.

Various implementations include an assembly including an introducer. The assembly is for use with a vacuum system and an esophageal positioning device. The esophageal positioning device includes a first segment and a second segment. The first segment has a central axis, and the second segment has a proximal end pivotally connected to the first segment and a distal end opposite and spaced apart from the proximal end. The second segment is pivotable about the first segment between a first position and a second position upon articulation. The distal end of the second segment is disposed along the central axis in the first position, and the distal end of the second segment is displaced from the central axis in the second position.

The introducer is sized to receive the esophageal positioning device. The introducer includes a soft outer tube and a tube tip. The soft outer tube is sized to pass through a mouth or nasal passage into an esophagus. The soft outer tube includes a longitudinal axis, a distal end, a proximal end, and a body. The body defines a plurality of radial vacuum holes spaced circumferentially around the longitudinal axis. The plurality of radial vacuum holes are in fluid communication with the vacuum system to apply a vacuum to an esophageal wall. The tube tip is located at the distal end of the outer tube.

A gap portion of the outer tube is defined along the longitudinal axis between the tube tip of the introducer and the distal end of the second segment of the esophageal positioning device when the esophageal positioning device is disposed within the introducer. The gap portion defines one or more of the radial vacuum holes. The distal end of the second segment remains a same distance from the proximal end of the second segment in the first position and the second position.

In some implementations, the gap portion defines a higher density of radial vacuum holes than any other portion of the body of the introducer.

In some implementations, a density of radial vacuum holes is highest adjacent the distal end of the outer tube, and the density of radial vacuum holes gradually decreases along the longitudinal axis in a direction from the distal end of the outer tube toward the proximal end of the outer tube.

In some implementations, the body of the outer tube has an end portion as measured along the longitudinal axis from the tube tip to the pivotal connection between the first segment and the second segment of the esophageal positioning device when the esophageal positioning device is disposed within the introducer. Only the end portion of the body of the outer tube defines the plurality of radial vacuum holes.

In some implementations, a length of the gap portion of the outer tube as measured along the longitudinal axis is from 10 mm to 30 mm. In some implementations, the length of the gap portion of the outer tube as measured along the longitudinal axis is 28 mm. In some implementations, a length of the second segment is 40 mm or more.

In some implementations, the introducer further includes one or more eyelets extending radially outward from the outer tube. Each of the one or more eyelets defines an eyelet opening and the eyelet openings of each of the one or more eyelets are axially aligned with each other along the outer tube.

In some implementations, the introducer further includes one or more occlusion balloons extending radially outward from the outer tube. The one or more occlusion balloons are inflatable. In some implementations, the one or more occlusion balloons include a first occlusion balloon and a second occlusion balloon. The first occlusion balloon is disposed at the distal end of the outer tube, and the second occlusion balloon is disposed at a portion of the outer tube that is adjacent the pivotal connection between the first segment and the second segment of the esophageal positioning device when the esophageal positioning device is disposed within the introducer.

Various other implementations include a mechanical esophageal displacement system including an assembly. The assembly includes an introducer and an esophageal positioning device. The assembly is operatively coupled to a vacuum system.

The introducer is sized to receive an esophageal positioning device. The introducer includes a soft outer tube and a tube tip. The soft outer tube is sized to pass through a mouth or nasal passage into an esophagus. The soft outer tube includes a longitudinal axis, a distal end, a proximal end, and a body. The body defines a plurality of radial vacuum holes spaced circumferentially around the longitudinal axis. The plurality of radial vacuum holes are in fluid communication with the vacuum system to apply a vacuum to an esophageal wall. The tube tip is located at the distal end of the outer tube.

The esophageal positioning device includes a first segment and a second segment. The second segment has a central axis, a proximal end pivotally connected to the first segment, and a distal end opposite and spaced apart from the proximal end. The second segment is pivotable about the first segment between a first position and a second position upon articulation.

A gap portion of the outer tube is defined along the longitudinal axis between the tube tip of the introducer and the distal end of the second segment of the esophageal positioning device when the esophageal positioning device is disposed within the introducer. The gap portion defines one or more of the radial vacuum holes. The second segment includes a distal band laminate assembly housing a plurality of distal bands in which the distal ends of the bands are slidable along the central axis relative to each other.

In some implementations, the gap portion defines a higher density of radial vacuum holes than any other portion of the body of the introducer.

In some implementations, a density of radial vacuum holes is highest adjacent the distal end of the outer tube, and the density of radial vacuum holes gradually decreases along the longitudinal axis in a direction from the distal end of the outer tube toward the proximal end of the outer tube.

In some implementations, the body of the outer tube has an end portion as measured along the longitudinal axis from the tube tip to the pivotal connection between the first segment and the second segment of the esophageal positioning device when the esophageal positioning device is disposed within the introducer. Only the end portion of the body of the outer tube defines the plurality of radial vacuum holes.

In some implementations, a length of the gap portion of the outer tube as measured along the longitudinal axis is from 10 mm to 30 mm. In some implementations, the length of the gap portion of the outer tube as measured along the longitudinal axis is 28 mm. In some implementations, length of the second segment is 40 mm or more.

In some implementations, the introducer further includes one or more eyelets extending radially outward from the outer tube. Each of the one or more eyelets defines an eyelet opening, and the eyelet openings of each of the one or more eyelets are axially aligned with each other along the outer tube.

In some implementations, the introducer further includes one or more occlusion balloons extending radially outward from the outer tube. The one or more occlusion balloons are inflatable. In some implementations, the one or more occlusion balloons include a first occlusion balloon and a second occlusion balloon. The first occlusion balloon is disposed at the distal end of the outer tube, and the second occlusion balloon is disposed at a portion of the outer tube that is adjacent the pivotal connection between the first segment and the second segment of the esophageal positioning device when the esophageal positioning device is disposed within the introducer.

Various other implementations include a method of using a mechanical esophageal displacement system. The method includes inserting an assembly described above into an esophagus of a patient via a mouth or nasal passage, coupling a vacuum system to the vacuum line hook up of the introducer, advancing an esophageal positioning device described above through the outer tube of the introducer, engaging the vacuum system to adhere a portion of the outer tube to an esophageal wall, and articulating the second segment about the first segment a selected angle from the first position to the second position.

In some implementations, the gap portion defines a higher density of radial vacuum holes than any other portion of the body of the introducer.

In some implementations, a density of radial vacuum holes is highest adjacent the distal end of the outer tube, and the density of radial vacuum holes gradually decreases along the longitudinal axis in a direction from the distal end of the outer tube toward the proximal end of the outer tube.

In some implementations, the body of the outer tube has an end portion as measured along the longitudinal axis from the tube tip to the pivotal connection between the first segment and the second segment of the esophageal positioning device when the esophageal positioning device is disposed within the introducer. Only the end portion of the body of the outer tube defines the plurality of radial vacuum holes.

In some implementations, a length of the gap portion of the outer tube as measured along the longitudinal axis is from 10 mm to 30 mm. In some implementations, the length of the gap portion of the outer tube as measured along the longitudinal axis is 28 mm. In some implementations, a length of the second segment is 40 mm or more.

In some implementations, the introducer further includes one or more eyelets extending radially outward from the outer tube. Each of the one or more eyelets defines an eyelet opening, and the eyelet openings of each of the one or more eyelets are axially aligned with each other along the outer tube.

In some implementations, the introducer further includes one or more occlusion balloons extending radially outward from the outer tube. The one or more occlusion balloons are inflatable. In some implementations, the one or more occlusion balloons include a first occlusion balloon and a second occlusion balloon. The first occlusion balloon is disposed at the distal end of the outer tube, and the second occlusion balloon is disposed at a portion of the outer tube that is adjacent the pivotal connection between the first segment and the second segment of the esophageal positioning device when the esophageal positioning device is disposed within the introducer.

The example method further includes advancing an esophageal positioning device through the outer tube of the introducer, in which the esophageal positioning device includes a handle, a first segment, a second segment, and an articulation driving mechanism. The first segment being coupled to the handle. The second segment being pivotally connected to the first segment. The articulation driving mechanism being configured to pivot the second segment about the first segment upon articulation.

The example method further includes snapping the handle of the esophageal positioning device to the vacuum port cap of the introducer, engaging the vacuum system to adhere a portion of the outer tube to an esophageal wall, and articulating the articulation driving mechanism to pivot the second segment about the first segment to a selected angle.

The details of one or more embodiments of the disclosure are set forth in the accompanying drawings and the description below. Other features, objects, and advantages of the disclosure will be apparent from the description, drawings, and from the claims.

DESCRIPTION OF DRAWINGS

To facilitate an understanding of and for the purpose of illustrating the present disclosure, exemplary features and implementations are disclosed in the accompanying drawings, it being understood, however, that the present disclosure is not limited to the precise arrangements and instrumentalities shown, and wherein similar reference characters denote similar elements throughout the several views, and wherein:

FIG. 5 is cross sectional view of the mechanical esophageal displacement system of FIG. 1;

FIG. 6 is zoomed in view of a portion of the mechanical esophageal displacement system of FIG. 1;

FIG. 16 shows a top view of a portion of the mechanical esophageal displacement system of FIG. 1, in which the view shows an esophageal positioning device being positioned in a first angular orientation;

FIG. 17 is a top, zoomed in, view of the portion of the esophageal positioning device of FIG. 16;

FIG. 18 shows a top view of a portion the mechanical esophageal displacement system of FIG. 1, in which the view shows an esophageal positioning device being positioned in a straight orientation;

FIG. 19 shows a top view of a portion of the mechanical esophageal displacement system of FIG. 1, in which the view shows an esophageal positioning device being positioned in a second angular orientation;

FIG. 20 is a top, zoomed in, view of the portion of the esophageal positioning device of FIG. 19;

DETAILED DESCRIPTION

Figure 1:
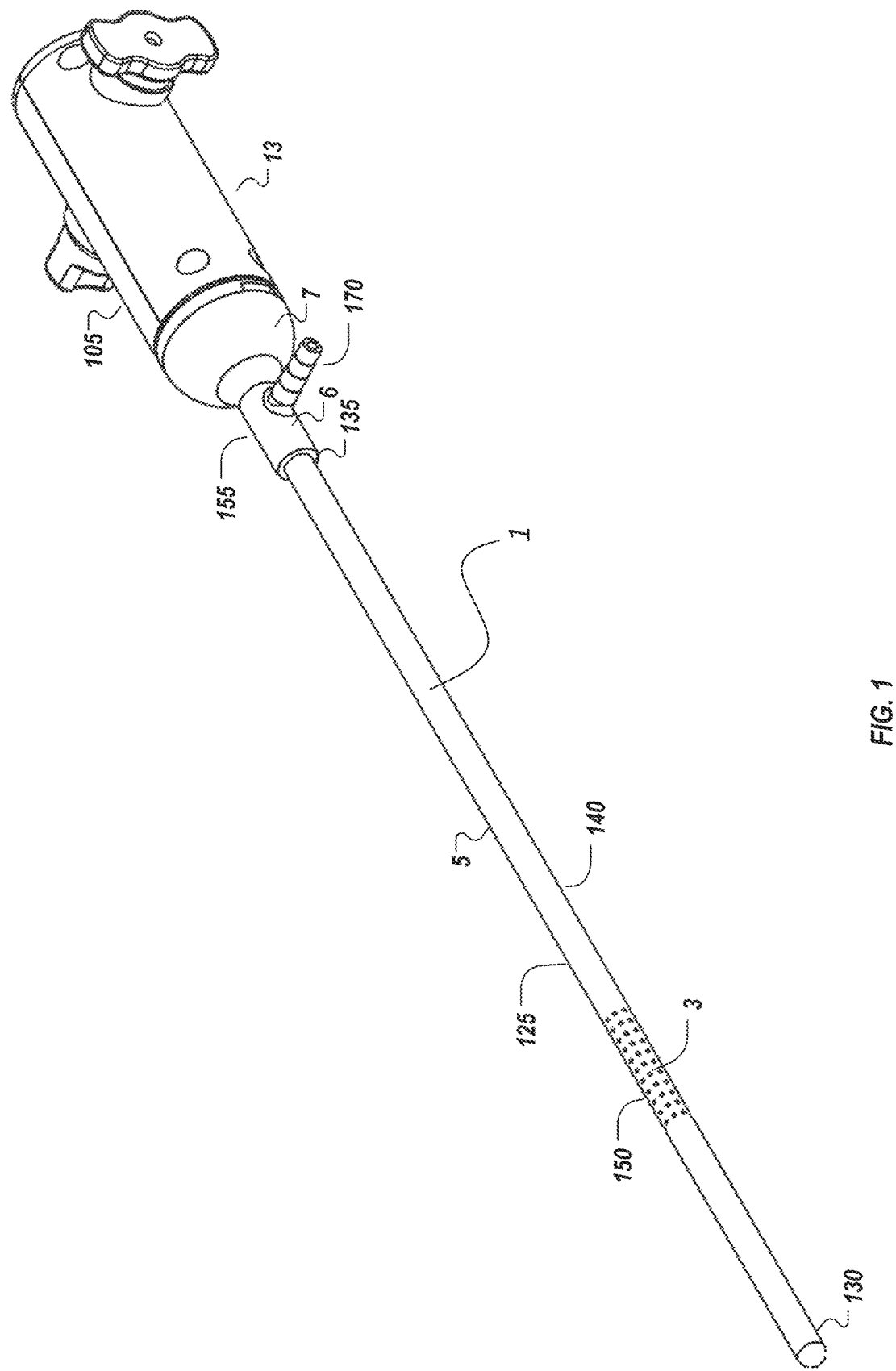
FIG. 1 is a perspective view of an example mechanical esophageal displacement system in accordance with the present disclosure.

The following is a description of several illustrations of the subject matter of Applicant's invention. Certain terminology is used herein for convenience only and is not to be taken as a limitation on the present invention. In the drawings, the same reference numbers are employed for designating the same elements throughout the several figures. A number of examples are provided, nevertheless, it will be understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed.

The present invention now will be described more fully hereinafter with reference to specific embodiments of the invention. Indeed, the invention can be embodied in many different forms and should not be construed as limited to the embodiments set forth herein; rather, these embodiments are provided so that this disclosure will satisfy applicable legal requirements.

FIGS. 1-25 show an example of a mechanical esophageal displacement system 1 in accordance with the present disclosure for mechanically displacing an esophagus during a medical procedure via vacuum suction adherence of a segment of the esophagus. As shown in FIGS. 1 and 5, the example mechanical esophageal displacement system 1 includes an assembly 5 and an esophageal positioning device 13, in which the assembly 5 is operatively coupleable to a vacuum system (not shown). In some embodiments, the assembly 5 is a disposable component of the mechanical esophageal displacement system 1, in which the assembly 5 includes one or more disposable pieces that can be removed and or replaced after a medical procedure. As will be discussed in further detail below, in some embodiments the esophageal positioning device 13 includes a handle 105, a first segment 110, a second segment 115, an articulation pivot pin 16, and an articulation driving mechanism 120. The first segment 110 and the second segment 115 may be linear structures for example.

FIGS. 2-5, 13, 25 show an example of an assembly 5 that is disposable in accordance with the present disclosure. The example assembly 5 includes an introducer 2 that is sized to receive the esophageal positioning device 13. The esophageal positioning device 13 may be a reusable component of the system 1, which is to be inserted into the lumen of the introducer 2 after the introducer is advanced down the esophagus of a patient 37. In some embodiments, however, the introducer 2 and the esophageal positioning device 13 are manufactured as a single device, and the single piece assembly 5 may be disposable or designed to be sterilized for repeated uses. The patient 37 may be a human or other animal.

Figure 2:
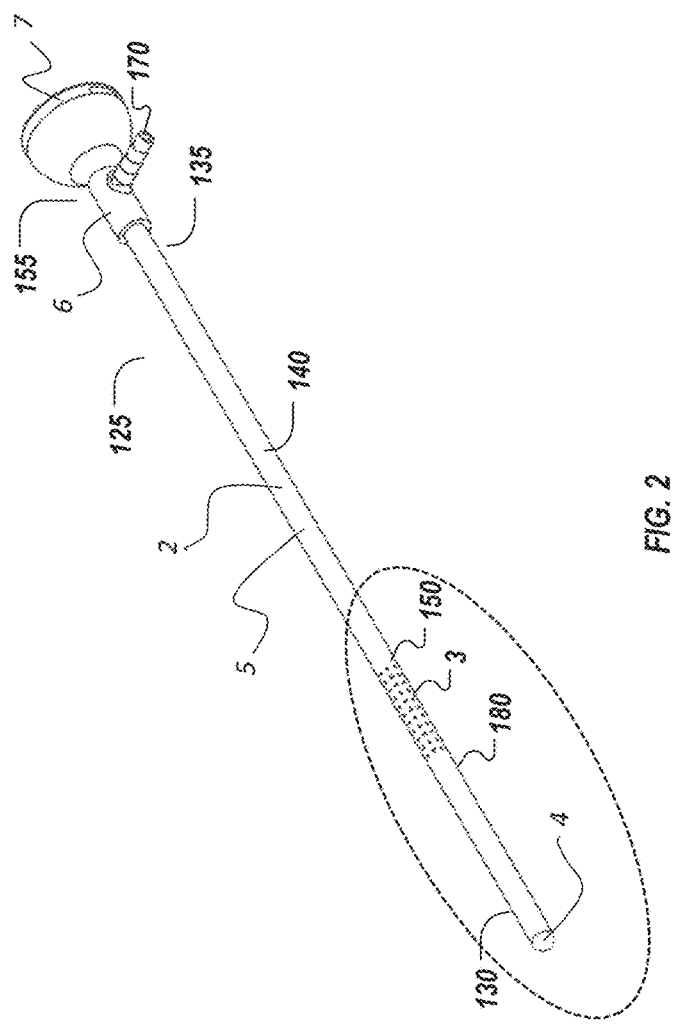
FIG. 2 is a perspective view of an example assembly of the mechanical esophageal displacement system of FIG. 1 in accordance with the present disclosure.
Figure 3:
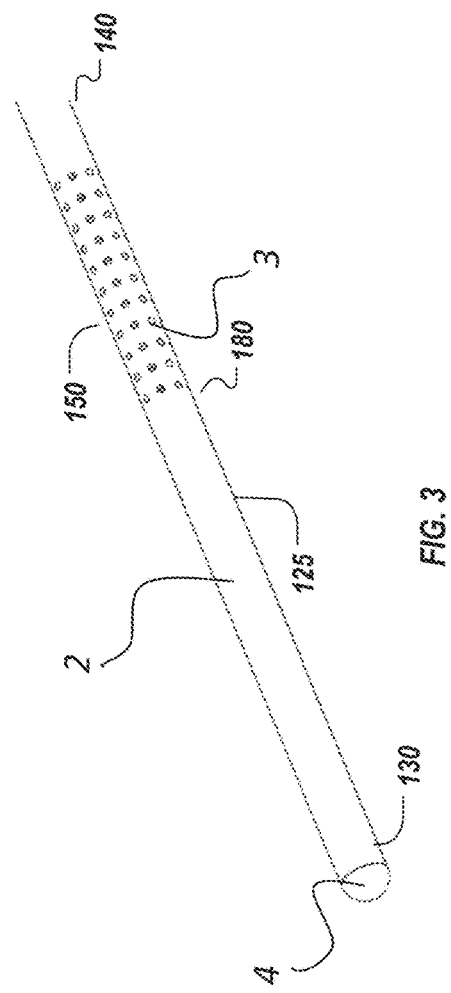
FIG. 3 is a perspective, zoomed in view, of a portion of the assembly of FIG. 2.
Figure 4:
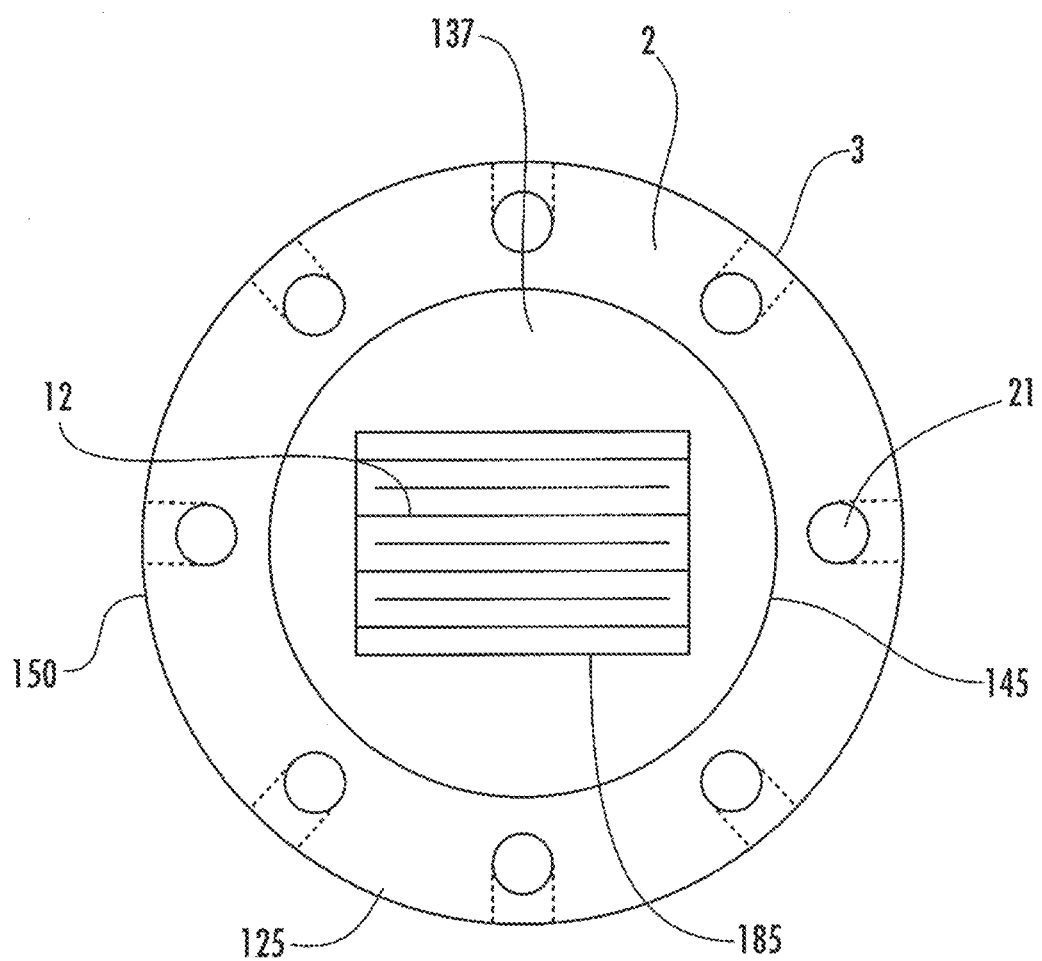
FIG. 4 is a cross sectional view of the assembly of FIG. 1.

As shown in FIG. 5, the introducer 2 includes a soft outer tube 125. In some embodiments the soft outer tube 125 is cylindrical. The soft outer tube 125 is sized such that it may pass through a mouth or nasal passage into an esophagus. The soft outer tube 125 includes a distal end 130, a proximal end 135, a lumen 137, and a body 140. In some embodiments the body 140 includes a contiguous inner surface 145. The body 140 of the outer tube includes a perforated outer surface 150 and along the length of the outer tube, and one or more internal vacuum passages 21 (see FIGS. 4 and 25) that extend a distance from the proximal end 135 towards the distal end 130 within the body 140 of the outer tube 125. In some embodiments, the perforated outer surface 150 includes a plurality of vacuum holes 3 spaced circumferentially around, and extending radially from, the soft outer tube 125, as seen in FIGS. 1-3. Because the plurality of vacuum holes 3 are spaced circumferentially around the soft outer tube 125, the plurality of vacuum holes 3 are located on multiple sides of the tube 125 and can suction the esophagus from multiple directions. The one or more internal vacuum passages 21 are in fluid communication with the plurality of vacuum holes 3 to apply a vacuum to an esophageal wall via the vacuum system. The outer tube 125, or portions thereof, can be made of, for example, a soft polymer like polyvinyl chloride (PVC) or silicone. The outer tube 125 is flexible enough to not add unnecessary stiffness to the system 1 to which the esophageal positioning device 13 would need to overcome, but not too flexible such that the outer tube 125 bunches up while inserting the introducer 2 into the esophagus. In some embodiments, the outer tube 125 includes a lubricious material coating (e.g., hydro-glide) to facilitate introduction into the esophagus and to minimize esophageal trauma.

While the outer tube 125 can be made of a single material, in some embodiments, a multi-durometer outer tube 125 is made of more than one material to achieve a desired stiffness at different portions along the outer tube 125. In some embodiments, the distal end 130 is made of a stiffer material, for example, a combination of silicone and polyurethane or other materials, while a portion between the distal end 130 and the proximal end 135 that includes a plurality of radial vacuum holes 3 is made of a more pliable material. The stiffer distal end 130 better facilitates introduction of the soft outer tube 125 into the esophagus. The more pliable material of the portion containing the plurality of radial vacuum holes 3 allow this portion of the soft outer tube 125 to collapse, creating a smaller diameter of the soft outer tube 125 and enhancing the collapse of the esophagus. Consequently, this moves the esophagus further away from the heart and provides better circumferential adherence of the esophagus to the soft outer tube 125.

In some embodiments, the assembly 5 could include a telescoping mechanism on at least a portion of the device to facilitate entry of the device into the esophagus. Once in the desired location within the esophagus, the telescoping portion could extend to deploy the entire device.

As noted above, a segment of the esophagus may be adhered to the introducer 2 via vacuum suction. To that end, the perforated outer surface 150 of the introducer 2 can include a plurality of radial vacuum holes 3 which may be positioned at various locations about the outer surface 150. In some embodiments, the plurality or radial vacuum holes 3 are positioned along the outer surface 150 starting at about between three to five inches from a tube tip 4 and span a length of about two inches from the starting location. The plurality of holes 3 are designed to be in fluid communication with the one or more internal vacuum passages 21 such that a vacuum system can create a vacuum between an esophageal wall and the outer tube 125 when the vacuum is coupled to the assembly 5 and turned on. Fluid communication may be direct or indirect. In some embodiments, the one or more internal vacuum passages 21 extend towards but not to the distal end 130. For example, in some embodiments the one or more internal vacuum passages 21 extend up to but not past the location of the most distal of the radial vacuum holes 3. In some embodiments, the one or more internal vacuum passages 21 extend through the entire length of the body 140. In some embodiments, the one or more internal vacuum passage 21 comprises one or more cylindrical rings that each or together define a cavity that are axially aligned with the lumen 137 (not shown). In some embodiments, the body 140 does not include one or more internal vacuum passages 21, but rather the plurality of radial vacuum holes 3 are in fluid communication with the lumen 137 and the vacuum is applied to the lumen 137 to create a vacuum between the esophageal wall and the outer tube 125. Any suitable vacuum system may be used that is able to provide sufficient suction to adhere a portion of the outer tube 125 to a portion of the esophageal wall. One suitable example vacuum system is a vacuum pump that provides a suction of 300 millimeters of mercury. In some embodiments, the mechanical esophageal displacement system 1 includes a feedback mechanism, such as a manometer, to confirm that a vacuum seal has been formed along the esophagus by measuring the change in pressure in the system.

As shown in FIGS. 1-3, 5, and 13, the introducer 2 can include a tube tip 4 located at the distal end 130 of the outer tube 125. In some embodiments the tube tip 4 comprises a hard polymer tip having a soft, circular contour, in which the tip is bonded to the distal end 130 of the outer tube 125, in which the tube tip 4 is a closed structure. The tube tip 4 is shaped to not harm the esophagus as the tube tip 4 is designed to be in direct contact with the esophageal passageway. The tube tip 4 may comprise a half dome shape for example. In some embodiments, the tube tip 4 is a closed structure and not luminal.

As shown in FIGS. 1, 2, 5, 13, the assembly 5 can further includes a vacuum port 155 comprising a vacuum port body 6 and a vacuum port cap 7. In some embodiments, the vacuum port cap 7 is a hard polymer cap that is bonded to the vacuum port body 6. The vacuum port cap 7 can further include a snap feature geometry and a quick release hinge mechanism (not shown) in order to couple and de-couple the handle of the esophageal positioning device 13 to the proximal end 135 of the outer tube 125. In some embodiments, the vacuum port body 6 includes a vacuum line hook up 170 that is in fluid communication with the one or more internal vacuum passages 21. The vacuum port body 6 may be bonded to both the introducer 2 and the vacuum port cap 7 to create an air tight seal. In some embodiments, the body 6 further includes a vacuum port valve and a lever (not shown), in which the lever may control the vacuum system.

In some embodiments, the introducer 2 further includes a plurality of radiopaque markers (not shown) located proximal to a location 180 where the pivot pin 16 would reside within the introducer 2. In some embodiments, the plurality of radiopaque markers span distally along or within the outer tube 125 of the introducer 2 from the location 180 of about where the pivot pin 16 would reside to the location of the tube tip 4. In some embodiments the plurality of radiopaque markers span a distance of about four to six centimeters from the tube tip 4. In some embodiments the radiopaque markers are throughout the outer tube 125.

Figure 7:
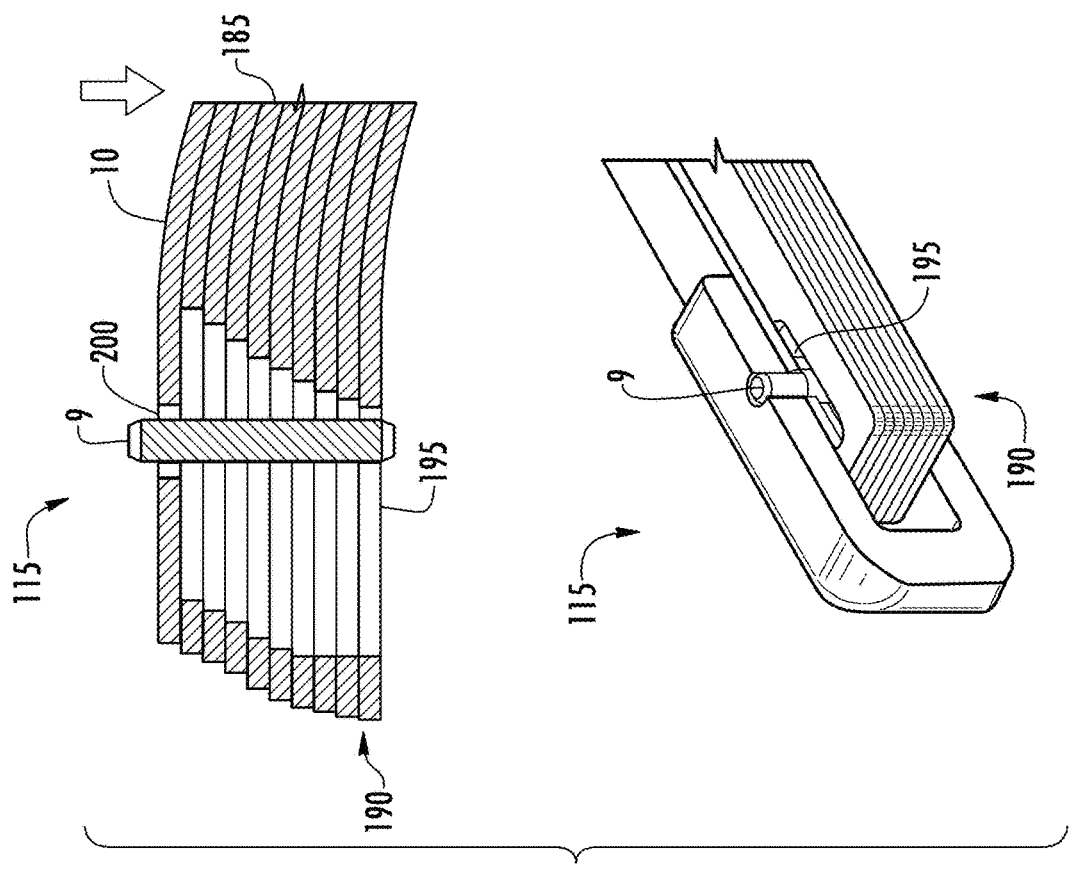
FIG. 7 is a perspective view a portion of the mechanical esophageal displacement system of FIG. 1.
Figure 8:
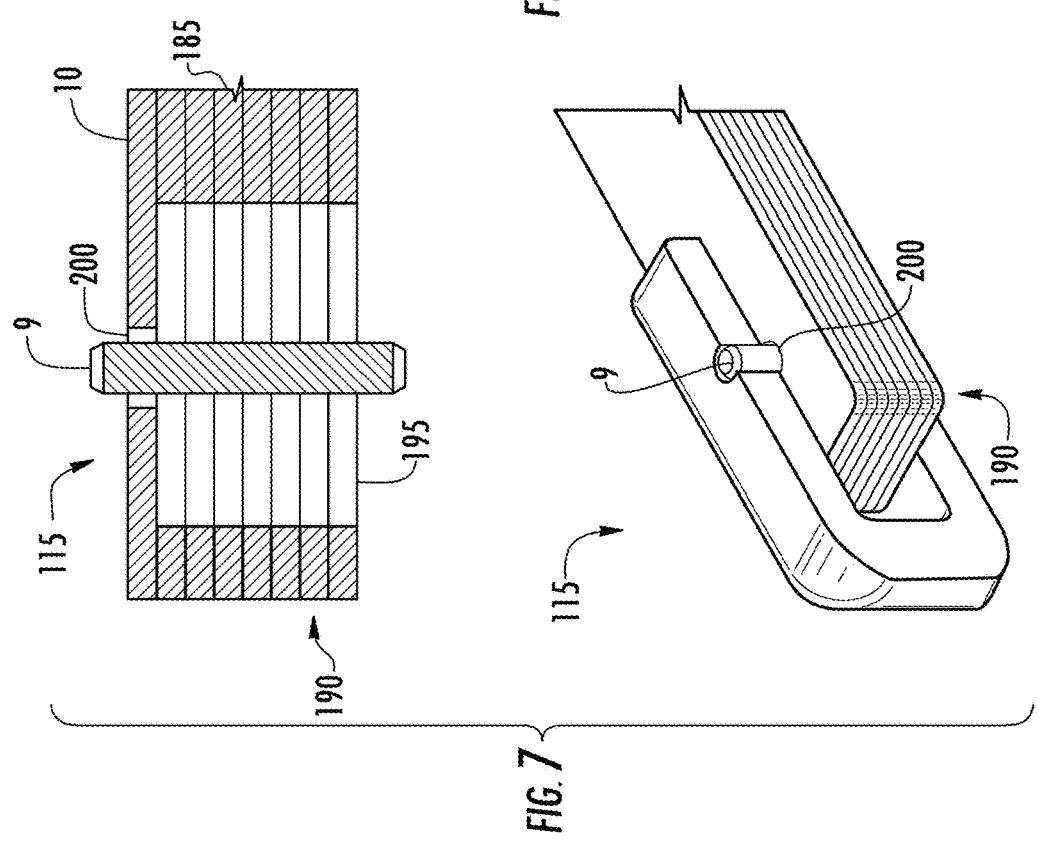
FIG. 8 is a perspective view a portion of the mechanical esophageal displacement system of FIG. 1.
Figure 9:
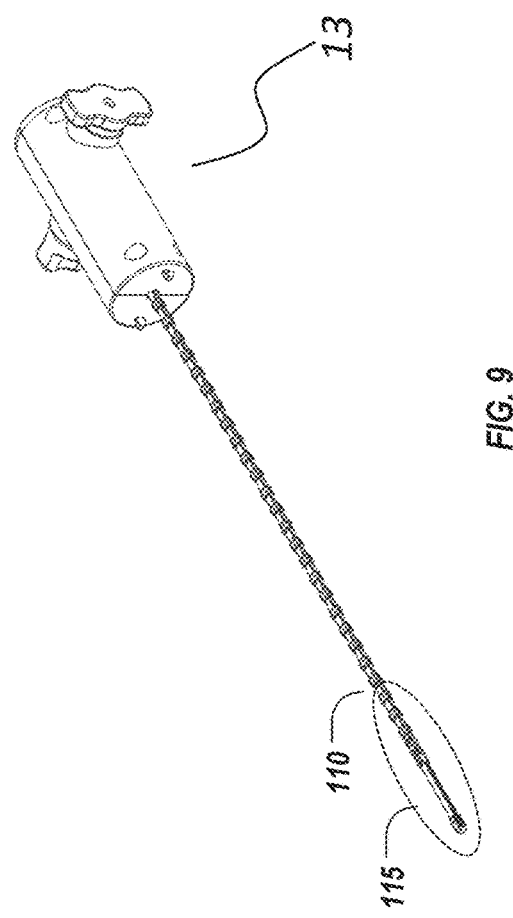
FIG. 9 is perspective view of an example esophageal positioning device of the mechanical esophageal displacement system of FIG. 1.
Figure 10:
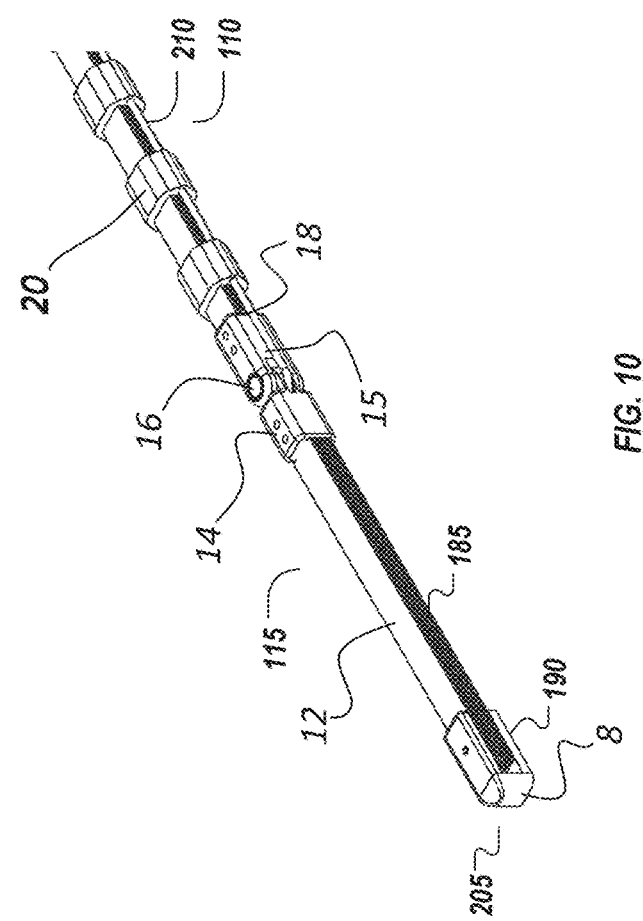
FIG. 10 is a perspective, zoomed in view, of a portion of the esophageal positioning device of FIG. 9.
Figure 11:
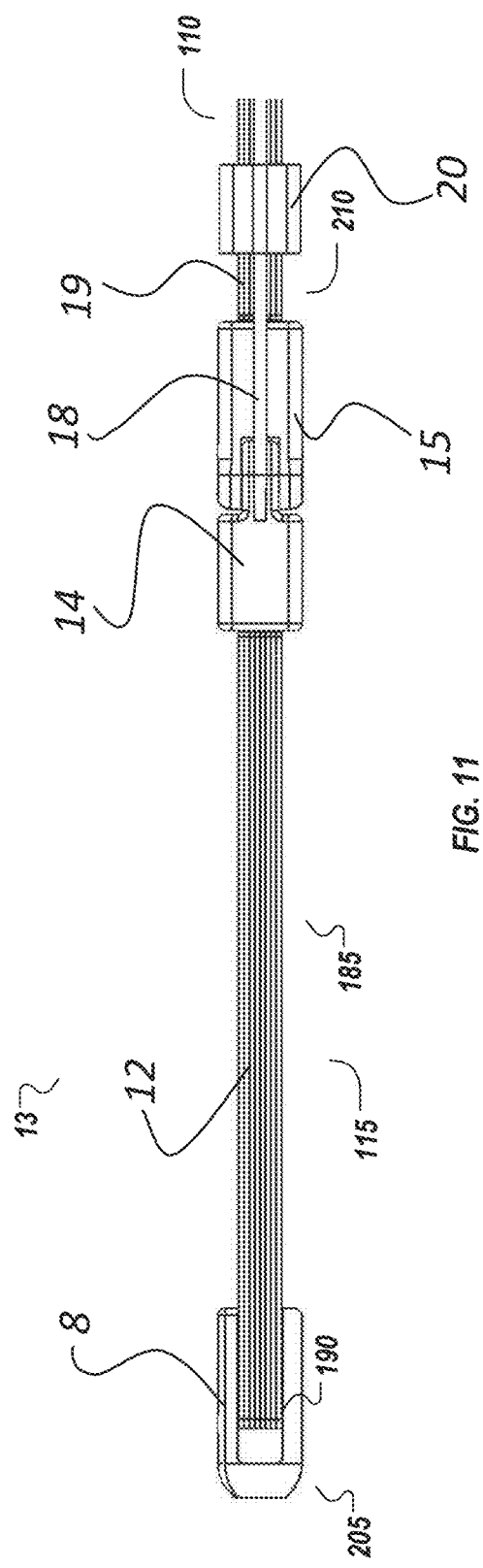
FIG. 11 is a side view of the portion of the esophageal positioning device of FIG. 10.
Figure 12:
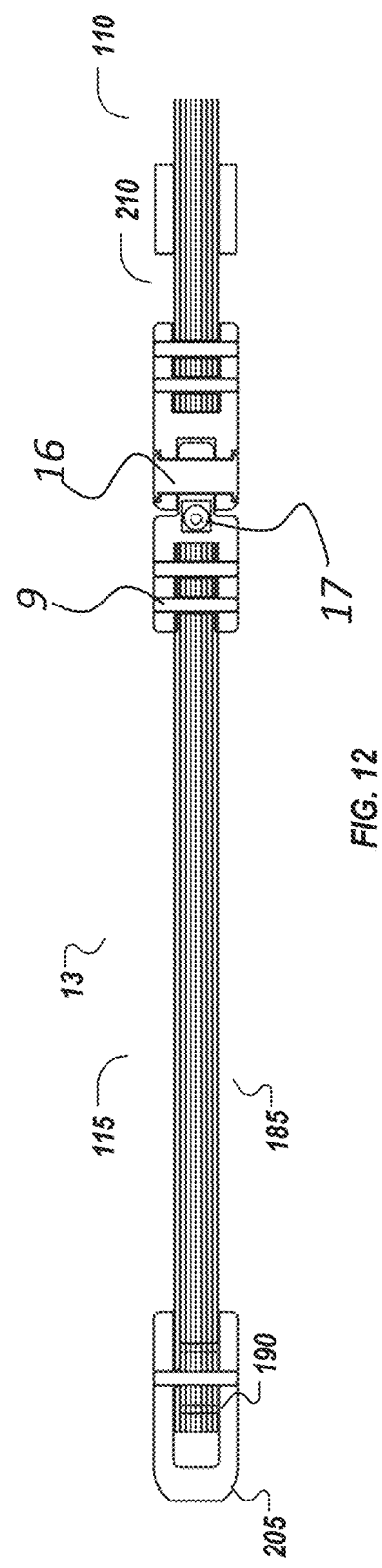
FIG. 12 is a top view of the portion of the esophageal positioning device of FIG. 10.

As noted above, in some embodiments the esophageal positioning device 13 includes a handle 105, a first segment 110, a second segment 115, an articulation pivot pin 16, and an articulation driving mechanism 120. In some embodiments, the second segment 115 is sized to displace the esophageal wall by about 4 centimeters upon articulation. In some embodiments the second segment 115 is between four to six centimeters long. As shown in FIGS. 4-21, the second segment 115 may comprise a distal band laminate assembly 12, a distal band guard 8, and a distal pivot retainer 14, in which the distal band assembly 12 houses a plurality of distal bands 185. As shown in FIGS. 7-8, the distal band guard 8 retains the distal band assembly 12 at a distal end 190 by a pin 9 that passes through the plurality of distal bands 185. The distal band assembly 12 may be made from various suitable materials, including for example, 300 or 400 series stainless steel or a hard polymer. The plurality of distal bands 185 may be made from spring steel for example. The distal pivot retainer 14 may be made of 300 or 400 series stainless steel or 17-4 stainless steel for example. The plurality of distal bands 185 may be assembled to the distal pivot retainer 14 by welding, using pins or bonding. The distal bands 185 may be rigidly attached to the distal pivot retainer 14 as the bands 185 are free to flex at the distal end 190.

As shown in FIGS. 7-8, in some embodiments, all but one of the distal bands 185 has a slot 195 at a distal end as to not interfere with the pin when the bands are being flexed. One distal band 10, either the top or outer band, includes a hole 200 rather than a slot 195, in which the hole 200 restricts the band 10 from sliding when the plurality of distal bands 185 are being flexed. The hole 200 further assists with locating the plurality of distal bands 185 of the distal band assembly 12. In some embodiments the distal guard 8 has a rounded tip 205 that is free of sharp edges to prevent damage to the outer soft tube 125 during insertion.

As shown in FIGS. 10-24, in some embodiments, the first segment 110 includes a proximal pivot retainer 15, an articulation drive cable 18, and a proximal band laminate assembly 19. The proximal band assembly 19 includes a plurality of proximal bands 210. The proximal pivot retainer 15 houses the proximal laminate band assembly 19. The proximal bands 210 can be rigidly attached to the proximal pivot retainer 15 as the proximal bands 210 are free to flex at a proximal end 215 in the handle 105. In some embodiments, the proximal pivot retainer 15 limits the distal pivot retainer 14 from articulating more than a selected angle to each side, for example 45 degrees, to prevent risk of damage to the esophagus due to excessive translation.

Figure 14:
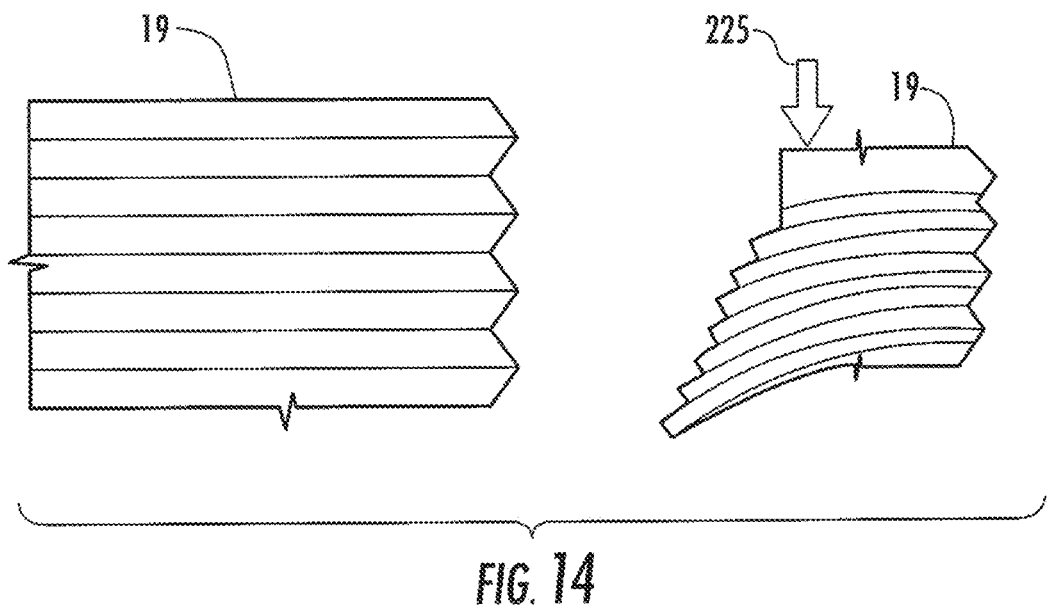
FIG. 14 is an illustrative diagram of a proximal band laminate assembly of the mechanical esophageal displacement system of FIG. 1 in accordance with the present disclosure, in which the view shows force being applied to the proximal band laminate assembly in the direction of the esophageal pathway.
Figure 15:
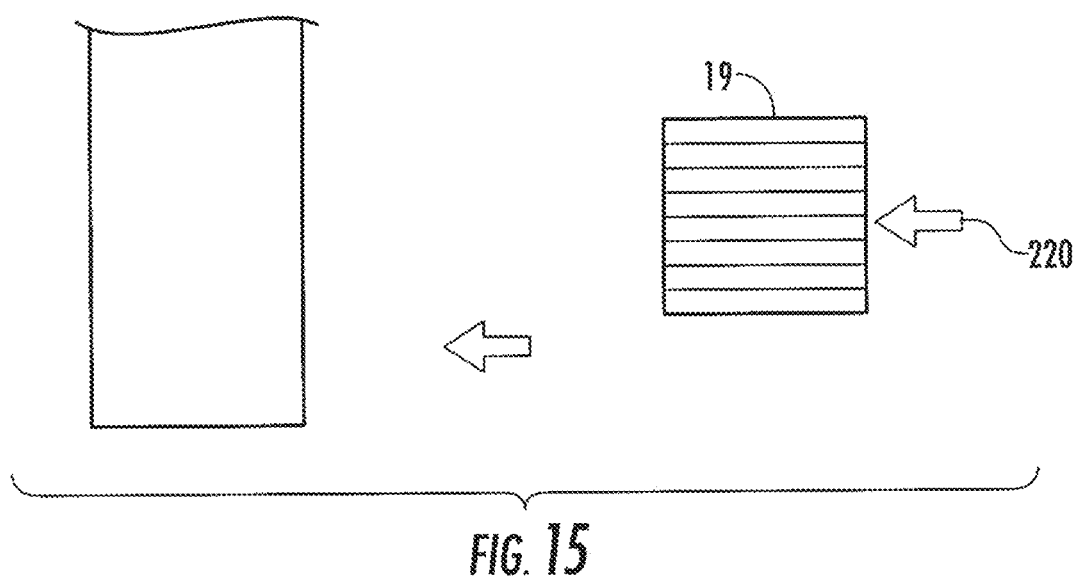
FIG. 15 is another illustrative diagram of a proximal band laminate assembly of the mechanical esophageal displacement system of FIG. 1 in accordance with the present disclosure, in which the view shows force being applied in a direction normal to the direction of the esophageal pathway.
Figure 21:
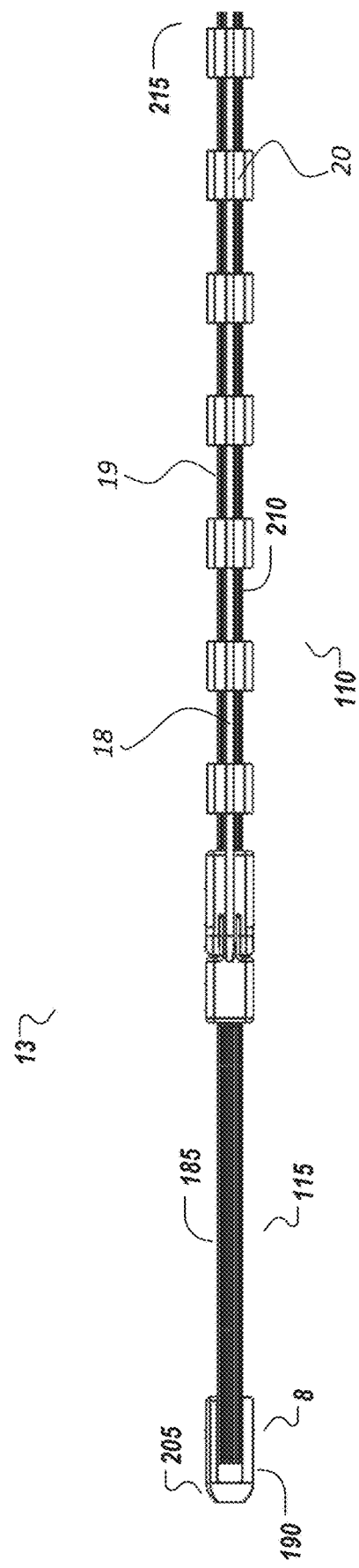
FIG. 21 is a top of a portion of the esophageal positioning device of the mechanical esophageal displacement system of FIG. 1 in accordance with the present disclosure.

As shown in FIGS. 14-15, the proximal band laminate assembly 19 may provide stiffness in a direction 220 that is normal to the direction of the esophageal pathway (FIG. 15) while maintaining flexibility in the direction 225 of the esophageal pathway. Flexibility may be maintained through the use of thin bands that are stacked on one and other (FIG. 14) to form a body that is think in the direction of the normal force provided by the esophagus (FIG. 15).

Similar to the distal band assembly 12, the proximal band laminate assembly 19 may be made from various suitable materials, including for example, 300 or 400 series stainless steel or a hard polymer. The plurality of proximal bands 210 may be made from spring steel for example. The articulation pivot pin 16 may be made from a 300 or 400 series stainless steel or 17-4 stainless steel, for example. The articulation pivot pin 16 connects both the distal pivot retainer 14 and proximal pivot retainer 15 and allows them to pivot. The articulation pivot pin 16 may be pressure fit into the proximal pivot retainer 15 and held in a loose fit by the distal pivot retainer 14.

As shown in FIGS. 10-12, and 17-20, in some embodiments the mechanical esophageal displacement system 1 further includes an articulation drive cable 18. This cable 18 can transmit an input force by a user from the handle 105 to the articulation pivot pin 16 to articulate the second segment 110 left or right 45 degrees from the neutral position wherein the distal band assembly 12 and the proximal band assembly 19 are parallel to each other. In some embodiments, the mechanical esophageal displacement system 1 includes a feedback mechanism that measures and displays the distance the device is articulated from its neutral position. In some embodiments, the cable 18 is approximately 0.024" in diameter and is made of a braided stainless steel or polymers such as UHMWPE, a liquid crystal polymer, or other high strength braided or monofilament polymers. In some embodiments, the mechanical esophageal displacement system 1 further includes an articulation cable crimp 17. As shown in FIGS. 16-20, the cable crimp 17 can be a small ball, compressed and friction fit onto a stainless steel braided cable 18. This crimp 17 provides a feature on the cable 18 that can interface with the distal pivot retainer 14 when pulled to the left or right in order to articulate the system 1. The ball may be compressed and friction fit onto the articulation cable 18 to provide an interfacing surface. In some embodiments, the articulation drive cable 18 is coupled to the distal pivot retainer 14 by welding in addition to or as an alternative to a cable crimp 17. Other types of mechanical of chemical fasters may be used to operatively couple the articulation drive cable 18 to the distal pivot retainer 18, such as being integrally formed, chemically bonded, or mechanically or magnetically joined.

In some embodiments, the mechanical esophageal displacement system 1 further includes a plurality of proximal band cable guides 20 that guide the articulation cable 18 from the handle 105 to the articulation pivot pin 16, wherein the plurality of proximal band cable guides 20 are evenly spaced along the plurality of proximal bands 210. The proximal band cable guides 20 may be welded or bonded to one or more of the proximal bands 210 so as to keep the proximal bands 210 aligned while still allowing the bands 210 to slip and translate independently when bent. The proximal band cable guides 20 assist with guiding the articulation drive cables 18 down the length of the esophageal positioning device 13. The proximal band cable guides 20 provide additional stiffness and structure to the proximal band laminate assembly 19 while still allowing the laminate band assembly 19 to bend.

Figure 22:
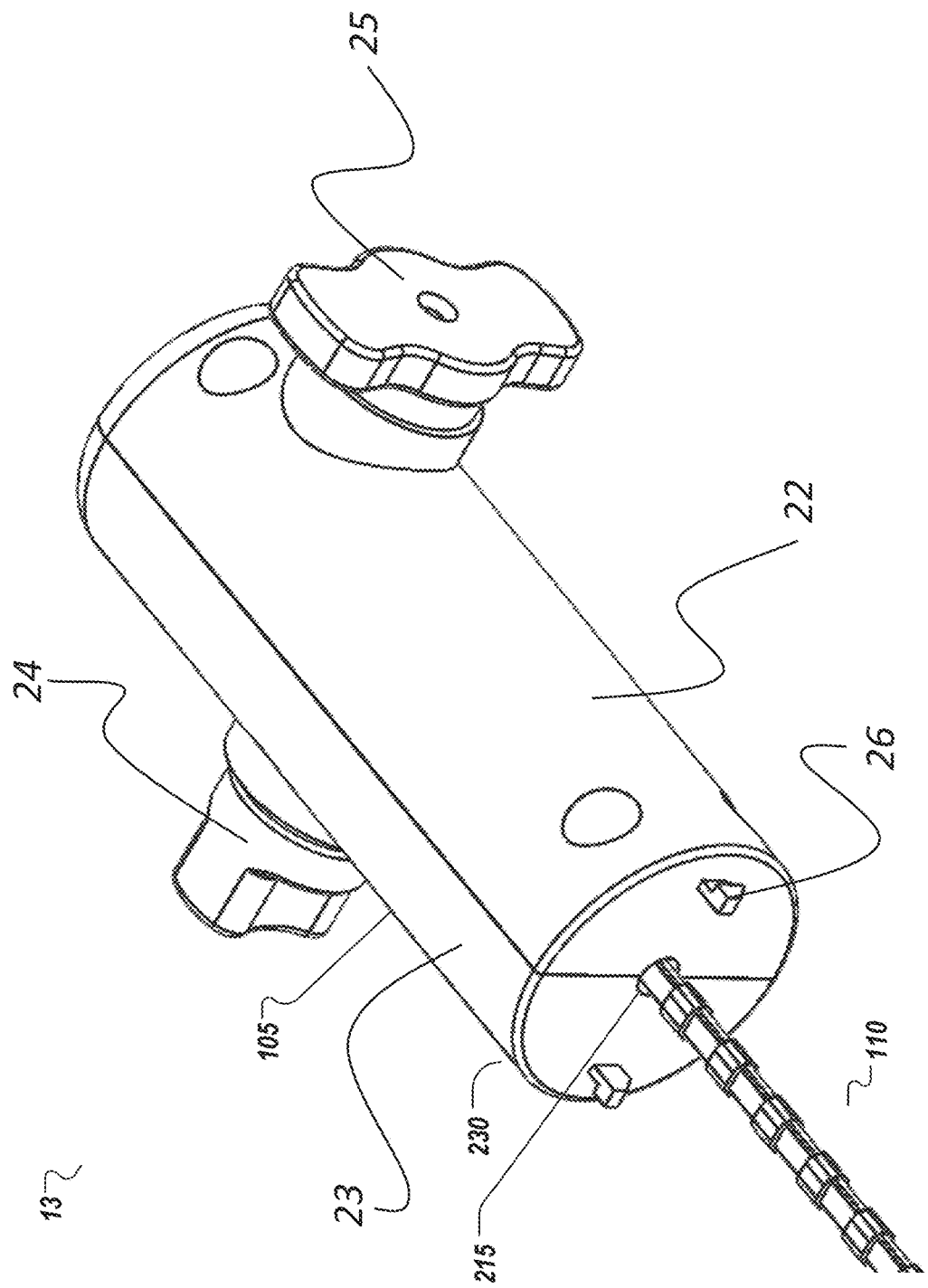
FIG. 22 is perspective view of the handle of the mechanical esophageal displacement system of FIG. 1.

As shown in FIGS. 1, 9, 13, 22-24, the handle 105 of the esophageal positioning device 13 may include a variety of components. As shown in FIG. 22, in some embodiments the handle 105 includes a two piece outer housing comprising an articulation handle case half 22 and a locking handle case half 23. In some embodiments, the articulation handle case half 22 may be made of a polymer or metal, and may be approximately 1.9" in diameter and approximately 5" long, for example. The articulation handle case half 22 may house the plurality of proximal bands 185, the articulation drive mechanism 120 as well as an articulation control knob 25. In some embodiments, the locking handle case half 23 may made of a polymer or metal, and may be approximately 1.9" in diameter and approximately 5" long, for example. The locking handle case half 23 may house the proximal bands 185, the articulation drive mechanism 120, and a locking control knob 24. The locking control knob 24 may be twisted to add friction to the system 1 as well as to completely lock the system 1 at a selected articulation angle. Twisting the locking control knob 25 in the opposite direction frees the articulation drive mechanism 120 to allow the articulation driving mechanism 120 to move freely. The knob 24 may be approximately one inch in overall diameter, for example. The articulation control knob 25 may be rotated in a first or second direction. In some embodiments, rotating the control knob in a clockwise direction may articulate the tube tip 4 of the assembly 5 to the right while rotating the control knob 25 counter clockwise may articulate the tube tip 4 of the assembly 5. The diameter of the articulation control knob 25 may be approximately two inches for example. As such, the articulating control knob 25 may articulate the second segment 115 to the right when rotated in a first direction and articulate the second segment 115 to the left when rotated in a second direction.

As shown in FIG. 22, the handle 105 of the esophageal positioning device 13 may include one or more snap hooks 26 that are located on the articulation handle case half 22 and or on the locking handle case half 23. The snap hooks 26 can be used to interface and couple the handle 105 to the vacuum port cap 7 of the assembly 5.

Figure 23:
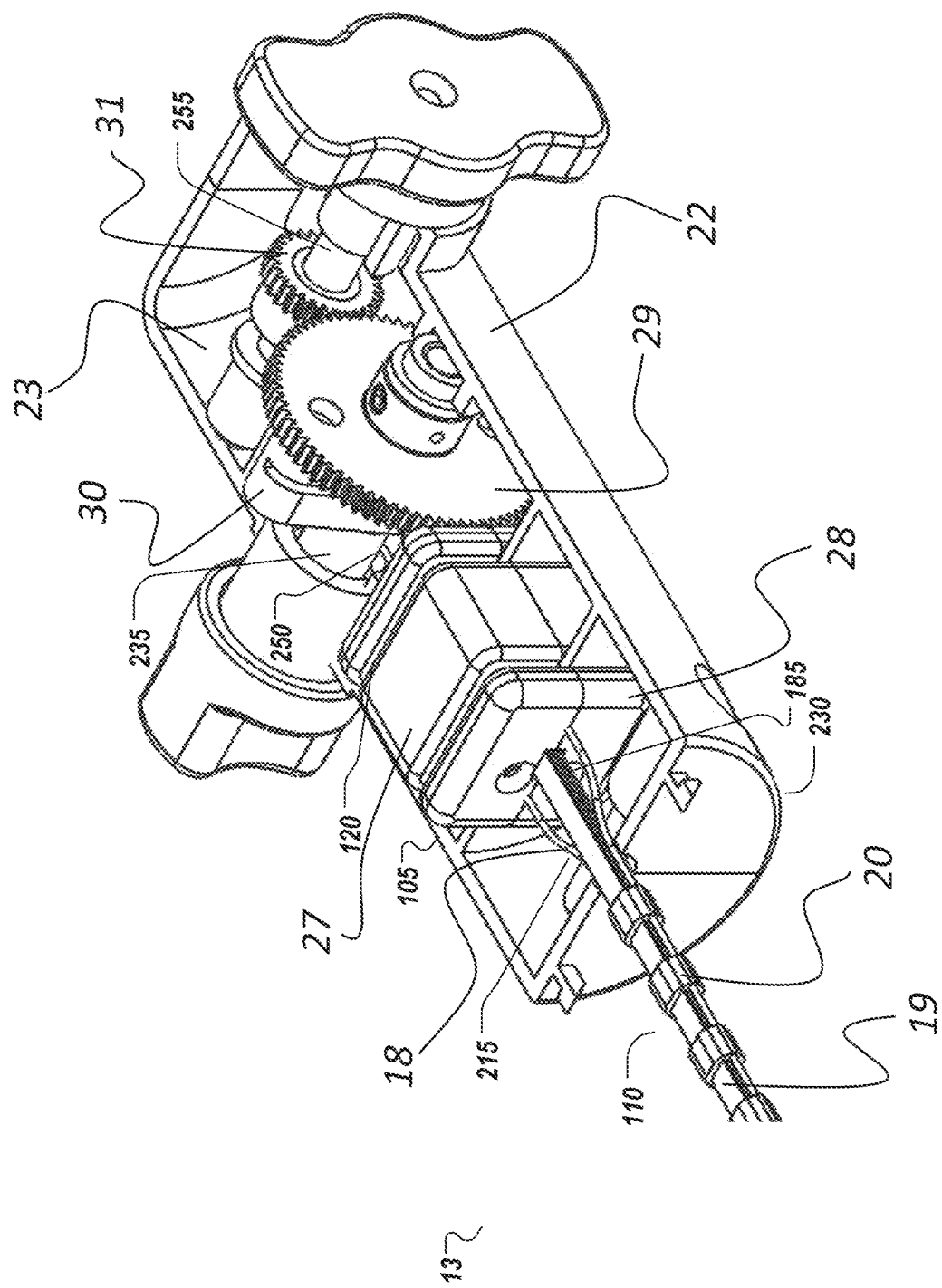
FIG. 23 is perspective view of the internal components of the handle of the mechanical esophageal displacement system of FIG. 1.
Figure 24:
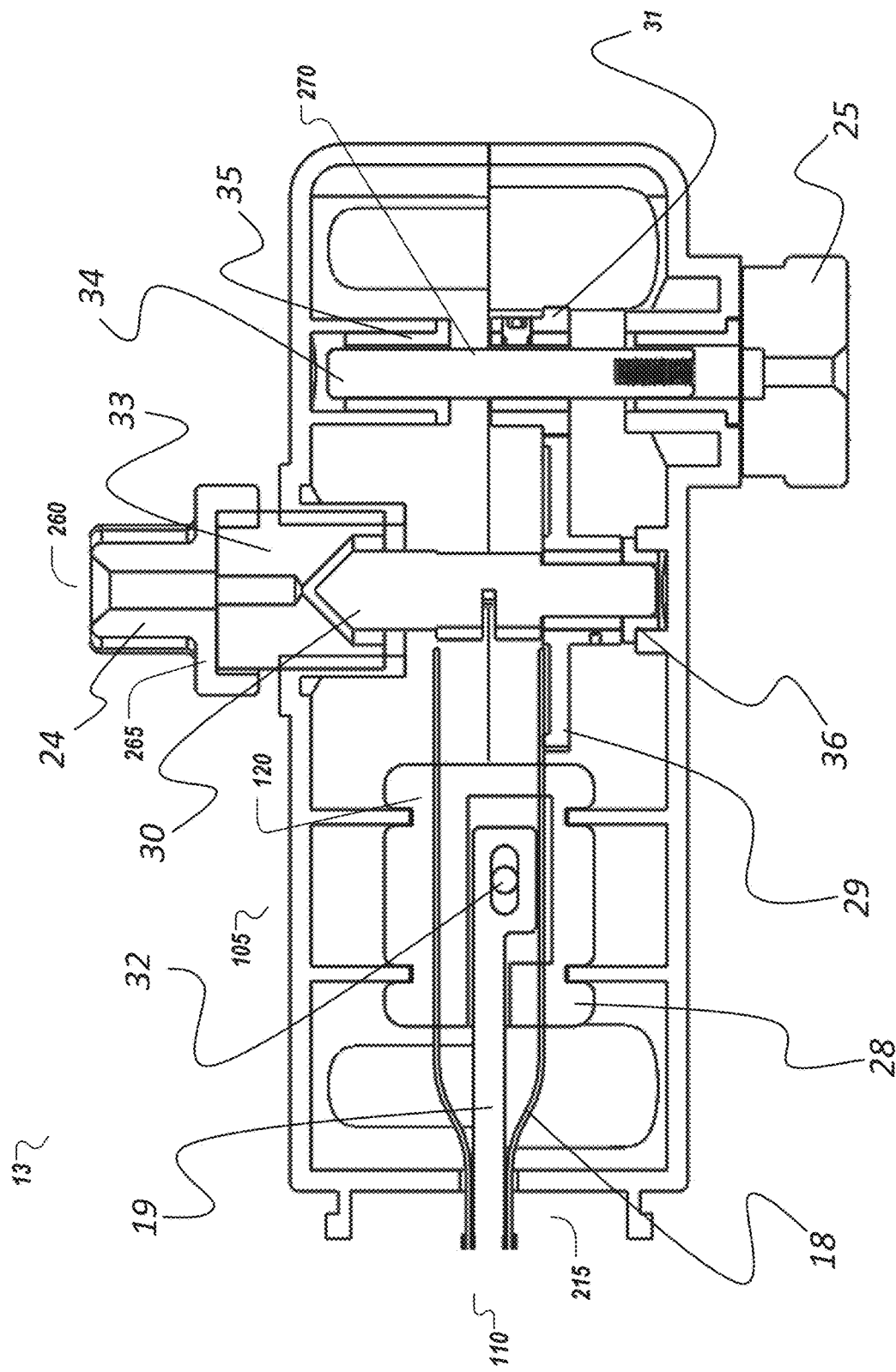
FIG. 24 is a side, cross sectional view of the internal components of the handle of FIG. 23.

As shown in FIG. 23-24, the handle 105 of the esophageal positioning device 13 may include a top handle band retainer 27, a bottom handle band retainer 28, a pulley gear 29, a cable pulley 30, an input gear 31, a proximal band handle retainer pin 32, a locking cone clutch 33, an articulation input shaft 34, an articulation input shaft bushing 35, and an articulation pulley shaft bushing 36, for example.

In some embodiments, the top and bottom handle band retainers 27, 28 house the proximal end 215 of the plurality of proximal bands 185 via pin, hole, and slot features of the proximal bands 185 to allow the bands 185 to translate while bending. The top and bottom retainers 27, 28 may be made of a polymer or aluminum, for example. The top and bottom retainers 27, 28 may be held in place together by ribs 230 found on the articulation handle case half 22 and on the locking handle case half 23.

In some embodiments, pulley gear 29 comprises a large gear that is attached to the cable pulley 30 via two pins. In some embodiments, the pulley gear 29 is concentric with the locking control knob 24 and a pulley shaft 235. In some embodiments, the pulley gear 29 is approximately two to three times larger in diameter than the diameter of the input gear 31.

In some embodiments, the articulation cables 18 are attached to the cable pulley 30 with the right side cable 18 being attached to a top pulley hole 250. The articulation cable 18 may be routed around the pins of the cable pulley 30.

In some embodiments, the input gear 31 is a small gear that is attached to an articulation control knob shaft 255 and to the pulley gear 29. The input gear 31 is used to lower the amount of input torque required by the user of the system 1 when articulating the esophageal positioning device 13. The input torque may be lowered by a factor of two to three, for example, based on a given ratio of input gear 31 to pulley gear 29. As such, in some embodiments the operator does not need to, or is restricted from, exerting more than 80 ounces per inch of torque to control the knobs 24, 25. For example, in some embodiments, a failsafe mechanism may be employed such that the articulation control knob 25 becomes locked upon an operator exerting a preset torque (e.g., more than 80 ounces per inch) to the articulation control knob 25. The lockout of the knob 25 may thus assist in avoiding injury to the operator.

In some embodiments, the proximal band handle retainer pin 32 interfaces with the proximal band laminate assembly 19, and the top and bottom handle band retainers 27, 28 to hold the proximal bands 185 in place. The proximal band handle retainer pin 32 align parts of the top and bottom handle band retainer 27, 28, when assembled together. The retain pin 32 aligns with the slots in the proximal bands 185 except for one, which allows the bands 185 to slip past one another when bending.

In some embodiments, the locking cone clutch 33 may be attached to the locking control knob 24 via a screw 260 and interfering ribs 265. The locking cone clutch 33 may include threads on an outer diameter that interface with threads of the locking handle case half 23. When the locking knob 24 is twisted, for example when twisted clockwise, the locking cone clutch 33 moves inward and interferes with a cone shaft on the cable pulley 30, which effectively slows and or locks the cable pulley 30 in its current position.

In some embodiments, the articulation input shaft 34 has a flat face that is, for example, D-shaped. The flattened face allows for interface with the input gear 31 via a set screw. The input shaft 34 may be approximately 0.25 inches in diameter for example. In some embodiments, the articulation input shaft bushing 35 allows the articulating input shaft 34 to freely spin. Similarly, in some embodiments, the articulation pulley shaft bushing 36 allows the articulating pulley shaft 34 to freely spin. The articulating input shaft bushing 35 and the articulating pulley shaft bushing 36 further assist in maintaining appropriate alignment of the handle 105 components.

In some embodiments, the esophageal positioning device 13 includes a clutch and or a force gauge system to limit the torque that may be exerted by a user. In some embodiments, a sensor (e.g., a thermistor or temperature sensor) is located at the distal end 190 of the esophageal positioning device 13. In some embodiments, the esophageal positioning device 13 includes multiple sensors (e.g., thermistors and/or temperature sensors) along the device to allow the measuring of temperature simultaneously at varied anatomic positions of the esophagus. In some embodiments, the thermistor, temperature, or other sensor is operatively connected to a computer, in which the computer displays a virtual image of the introducer 2 and or the esophageal positioning device 13 via a mapping screen. In some embodiments, the thermistor, temperature, or other sensor is used to display the device in a real-time imaging display (e.g., MRI, ultrasound (intracardiac, transesophageal, or transthoracic) or CT imaging), so to achieve three-dimensional imaging of the anatomy and the device. In some embodiments, the introducer 2 or the esophageal positioning device 13 includes a port to receive a gastrograffin injection or other material used to outline and visualize the esophagus on an x-ray. In some embodiments a ratcheting articulation control is provided such that one click of the ratcheting articulation control knob in a counter clockwise direction could causes 15 degrees of articulation to the left or 1.5 cm of translation to the left depending on which is desirable for the operator. In some embodiments audible clicks are provided as feedback to the operator as to the mount of tension being deliver to a knob. In some embodiments, a safety release mechanism is incorporated into the esophageal positioning device 13 so to prevent excessive force upon the esophagus.

In some embodiments, the esophageal positioning device 13 includes other imaging devices for use with visualizing techniques. Such imaging devices can include, for example, a fiber optic light source with a camera, ultrasound imaging (e.g., Doppler), etc. These imaging devices can be used to visualize the esophagus before, during, and after application of ablation energy and at other times during the procedure. The ultrasound imaging can be used, for example, to visualize and measure through the esophagus to view intracardiac objects such as catheters, transseptal techniques/equipment, evaluation of intracardiac thrombi, evaluation of intracardiac defects such as an atrial septal defect, visualize/measure pulmonary vein devices, visualize/measure mapping devices (e.g., multi-electrode baskets), visualize/measure the left atrial appendage and left atrial appendage closure devices, visualize/measure devices placed inside the pericardium, and other cardiac related products.

Figure 25:
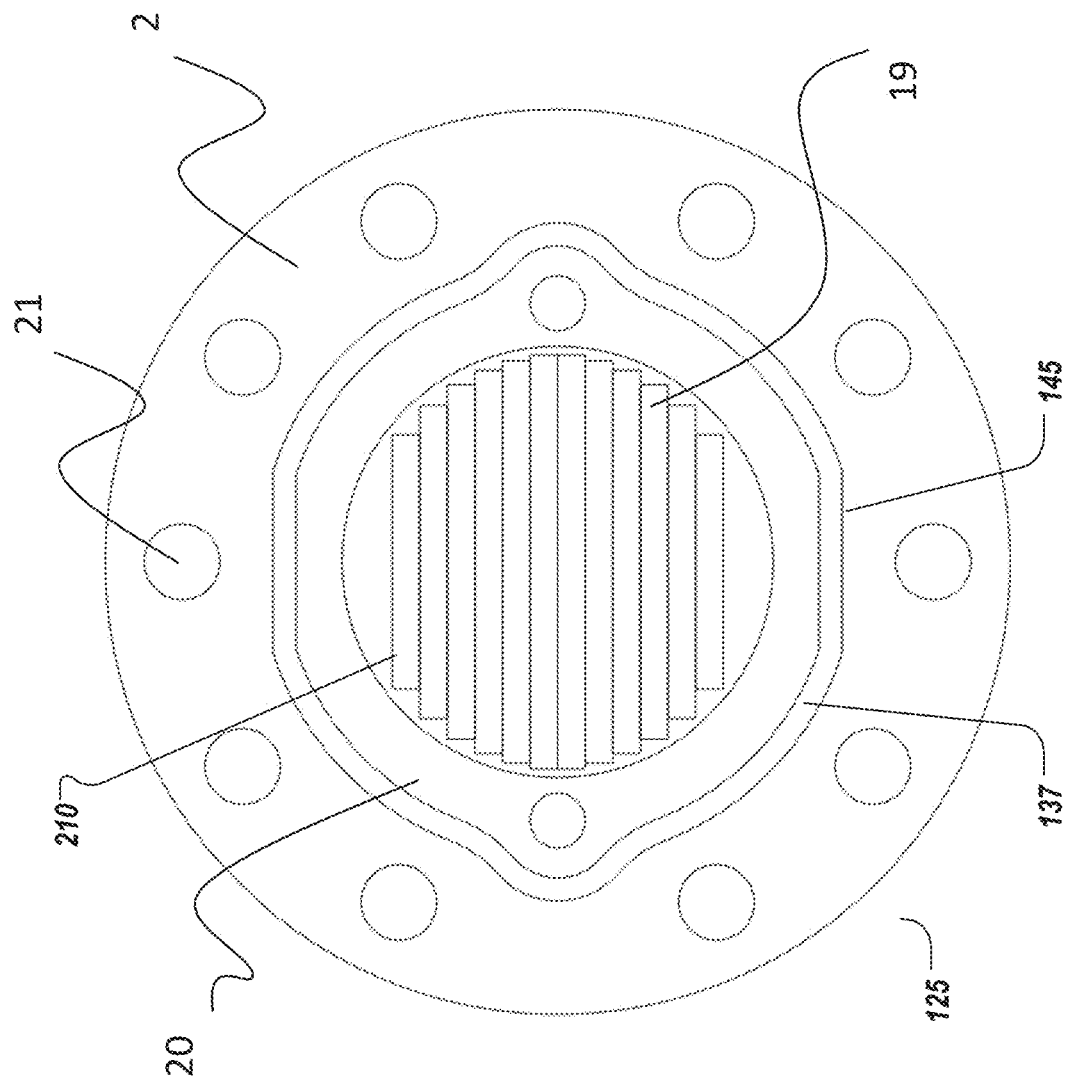
FIG. 25 is a cross sectional view of another example assembly of the mechanical esophageal displacement system of FIG. 1.

In some embodiments the band laminates of the distal or proximal band assemblies 12, 19 have differing widths. FIG. 25 shows an example of a proximal band assembly 19 having proximal bands 210 having differing widths. The widths of the distal or proximal bands 185, 210 can be shaped to maximize stiffness depending on profile shape of the outer tube 125 of the introducer 2. For example, if the profile shape the outer tube 125 of the introducer 2 is circular, the distal or proximal bands 185, 210 may be cut such that the profile of the bands 185, 210 take the shape of a circle. The use of differing widths can provide a more space efficient interaction between the bands 185, 210 and the outer tube of the introducer 2 or cable band guide 20. Moreover, cutting the bands of the proximal assembly 19 (or distal assembly 12) in different widths may increases the stiffness of the system 1 as the amount of material that is in contact with the inner surface of the outer tube or cable band guide 20 is increased.

Although many materials are disclosed for the various parts of the assembly 5, in some embodiments, all parts of the assembly 5 are made of non-ferrous materials to allow for use with advanced mapping systems or in an MRI procedure room.

Figure 13:
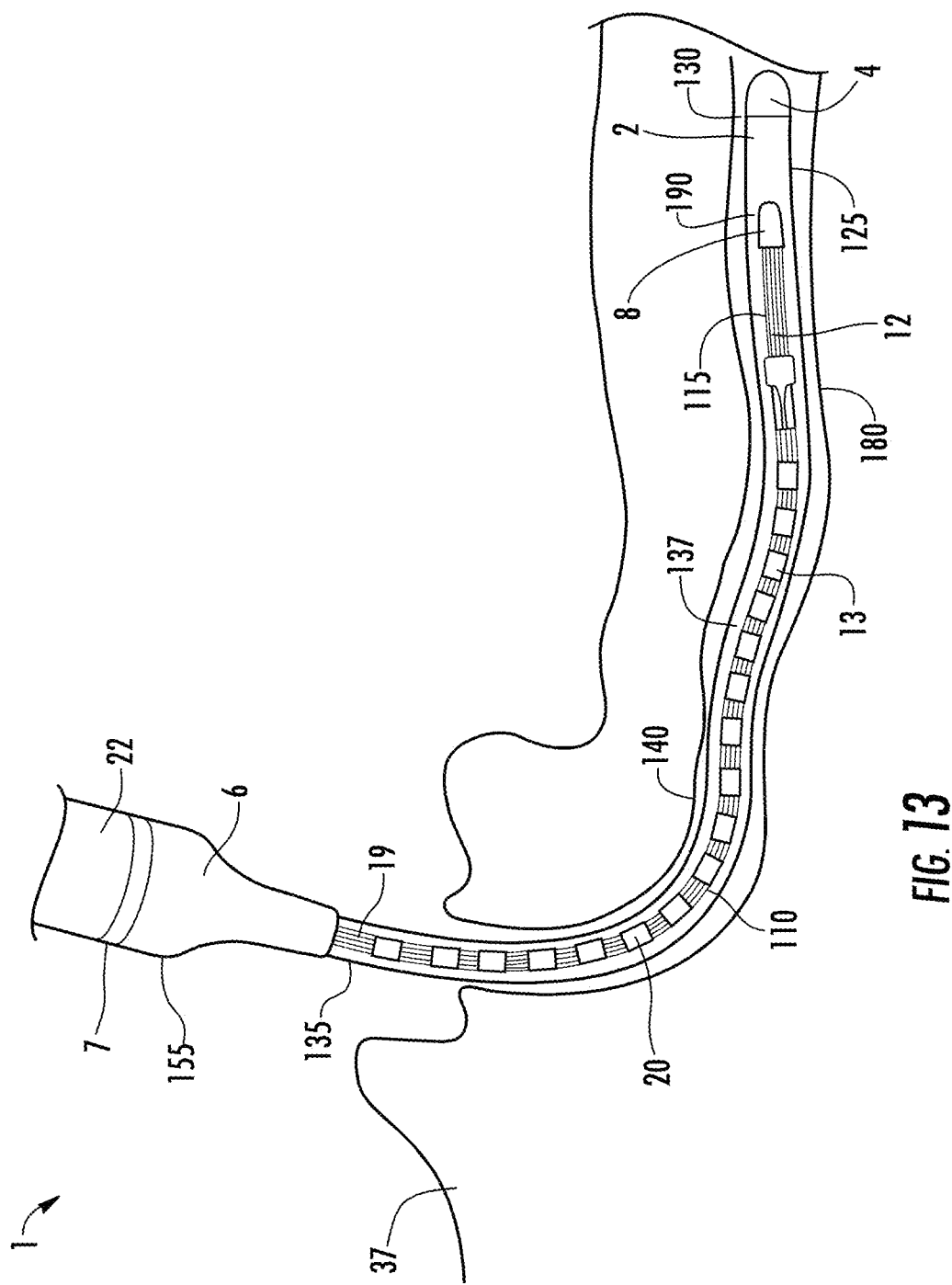
FIG. 13 is an illustrative diagram of the mechanical esophageal displacement system of FIG. 1, in which the view shows the mechanical esophageal displacement system being advanced down the esophagus of a patient.

Also provided are methods of using a mechanical esophageal displacement system 1. An example method includes inserting an assembly 5 into an esophagus of a patient 37 via a mouth or nasal passage (FIG. 13). The assembly 5 includes an introducer 2 having a soft cyclical outer tube 125, a vacuum port 155, and a tube tip 4. The soft outer tube 125 being sized to pass through a mouth or nasal passage of a patient into an esophagus, in which the soft outer tube 125 includes a distal end 130, a proximal end 135, a lumen 137 (see FIGS. 4 and 25), and a body 140. The body 140 of the outer tube 125 includes a perforated outer surface 150, and one or more internal vacuum passages 21 that extend a distance from the proximal end 135 towards the distal end 130 within the body 140 of the outer tube 125. In some embodiments, the perforated outer surface 150 includes a plurality of vacuum holes 3 spaced circumferentially around, and extending radially from, the soft outer tube 125, as seen in FIGS. 1-3. Because the plurality of vacuum holes 3 are spaced circumferentially around the soft outer tube 125, the plurality of vacuum holes 3 are located on multiple sides of the tube 125 and can suction the esophagus from multiple directions. The one or more internal vacuum passages 21 are in fluid communication with the plurality of vacuum holes 3 to apply a vacuum to an esophageal wall via the vacuum system. The tube tip 4 being located at the distal end 130 of the outer tube 125. The vacuum port 155 includes a vacuum port body 6, a vacuum line hook up 170, and a vacuum port cap 7. In some embodiments, the body includes a contiguous inner surface 145.

The example method further includes advancing an esophageal positioning device 13 through the outer tube of the introducer 2, in which the esophageal positioning device 13 includes a handle 105, a first segment 110, a second segment 115, an articulation pivot pin 16, and an articulation driving mechanism 120. The first segment 120 being coupled to the handle 105. The second segment 115 being pivotally connected to the first segment 110 via the articulation pivot pin 16. The articulation driving mechanism 120 being configured to pivot the second segment 115 about the first segment 110 upon articulation.

The example method further includes snapping the handle 105 of the esophageal positioning device 13 to the vacuum port cap 7 of the introducer 2, engaging the vacuum system to adhere a portion of the outer tube 125 to an esophageal wall, and articulating the articulation driving mechanism 120 to pivot the second segment 115 about the first segment 110 to a selected angle, for example an angle of about 45 degrees.

Figure 26:
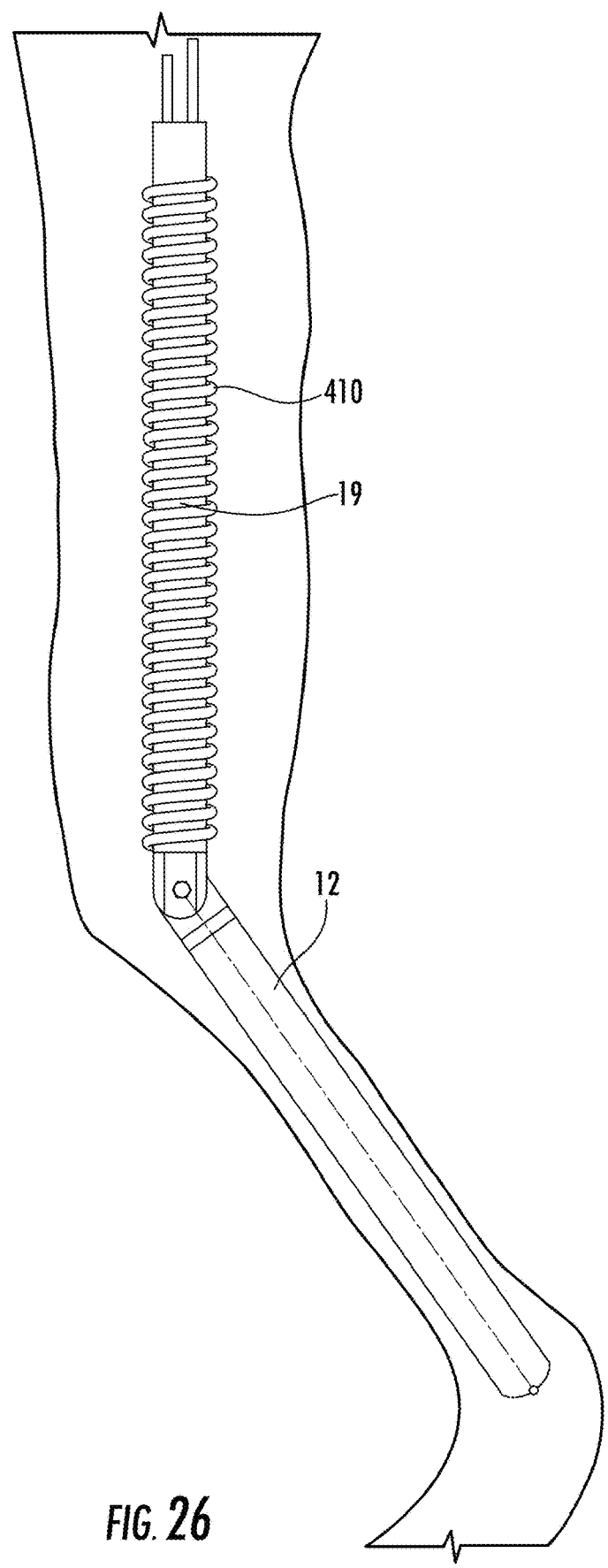
FIG. 26 is a top view of another example mechanical esophageal displacement system in accordance with the present disclosure.

FIG. 26 shows another example mechanical esophageal displacement system in accordance with the present disclosure. The mechanical esophageal displacement system includes a flexible coil 410 wrapped around a portion of the esophageal displacement device. Similar to the embodiment found in FIG. 1 above, the example mechanical esophageal displacement system of FIG. 26 can displace the esophagus about 4 centimeters, for example, 3.992 centimeters.

Figure 27:
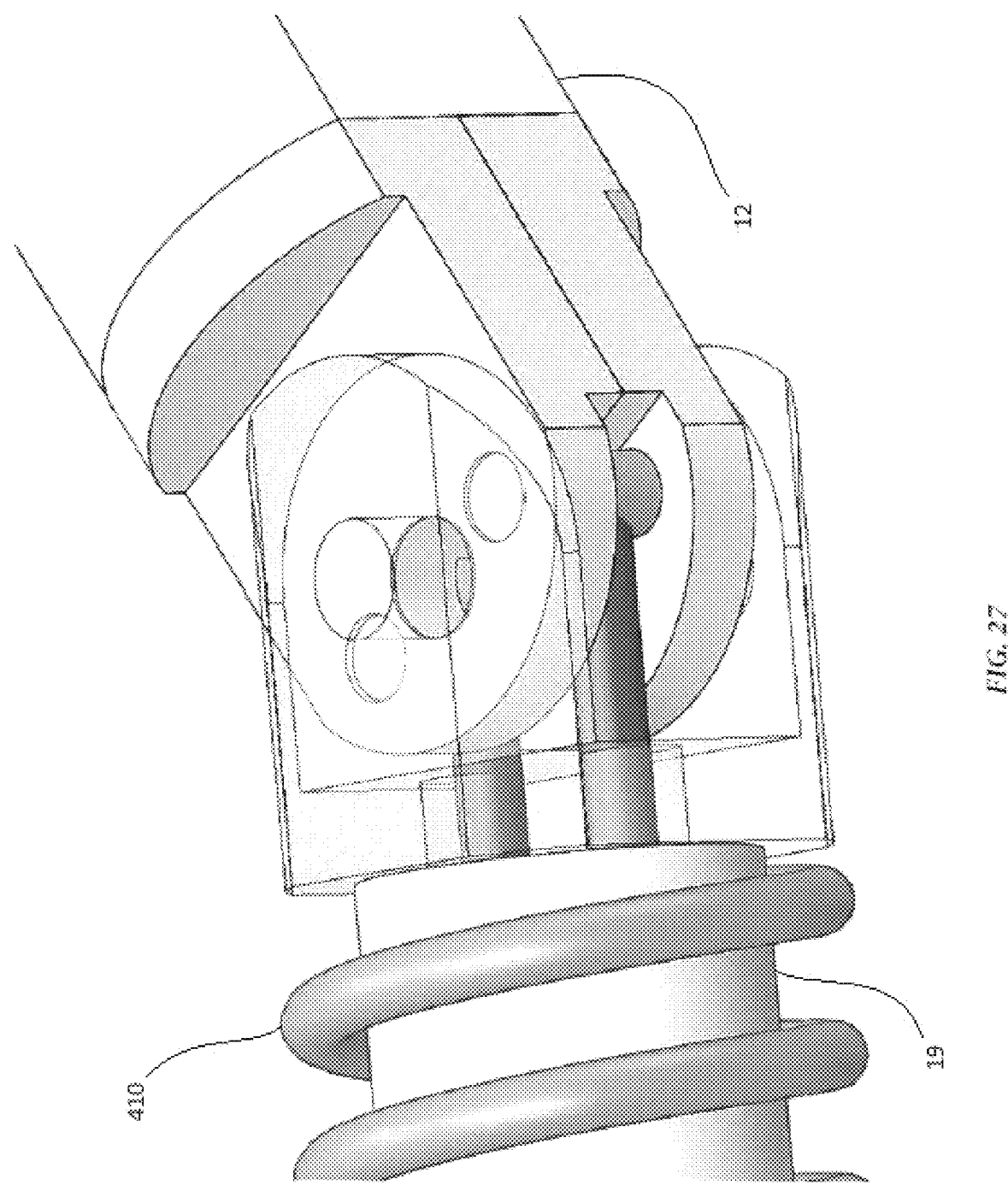
FIG. 27 is a perspective, zoomed in view of the example mechanical esophageal displacement system of FIG. 26.
Figure 28:
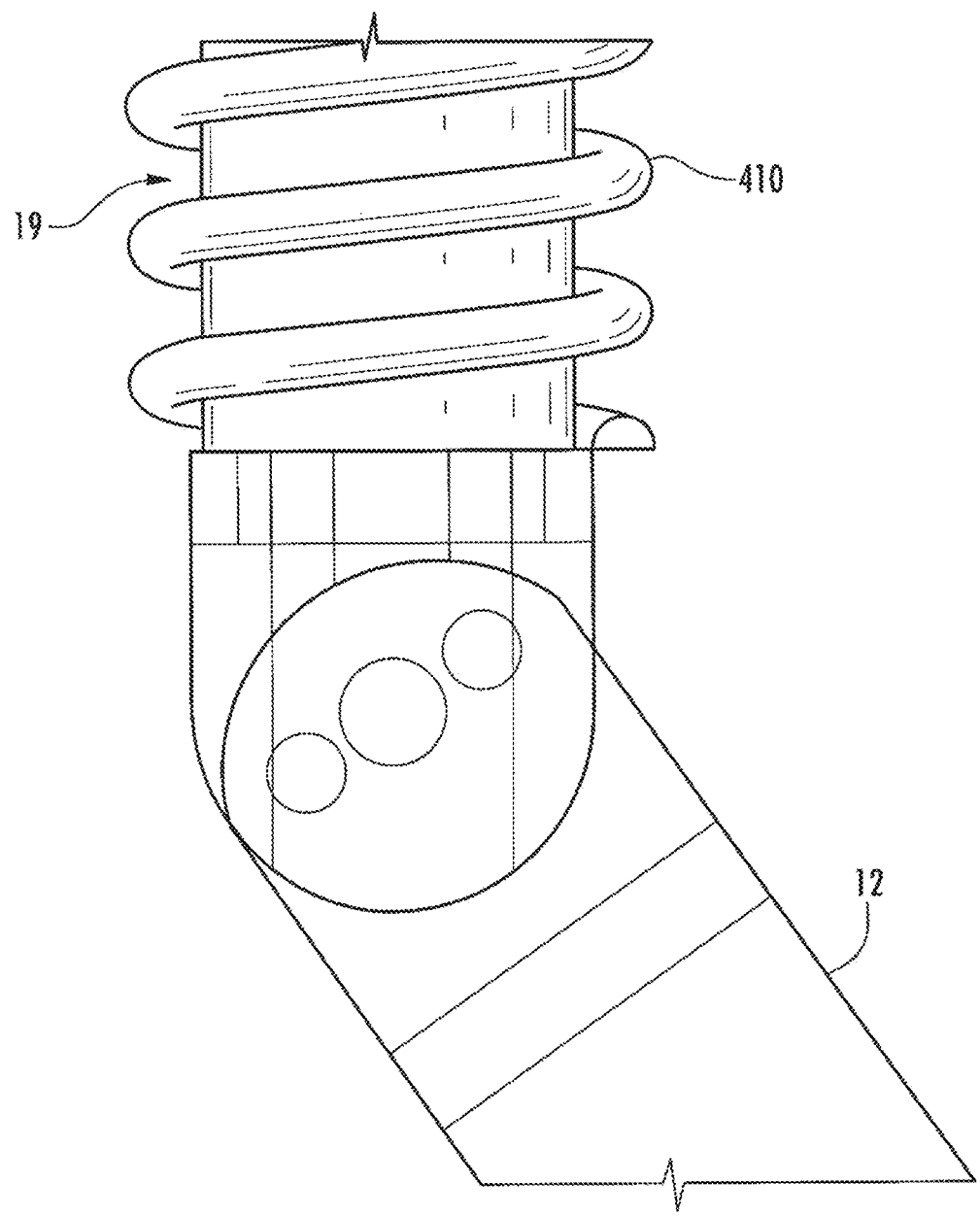
FIG. 28 is a top, zoomed in view of the example mechanical esophageal displacement system of FIG. 26

FIG. 27 is a perspective, zoomed in view of the example mechanical esophageal displacement system of FIG. 26. The view highlights an articulation pin that is operatively coupled to a coil to articulate the segments of the esophageal positioning device about the pin. FIG. 28 is a top, zoomed in view of the example mechanical esophageal displacement system of FIG. 26, in which the view highlights example dimensions.

Figure 29:
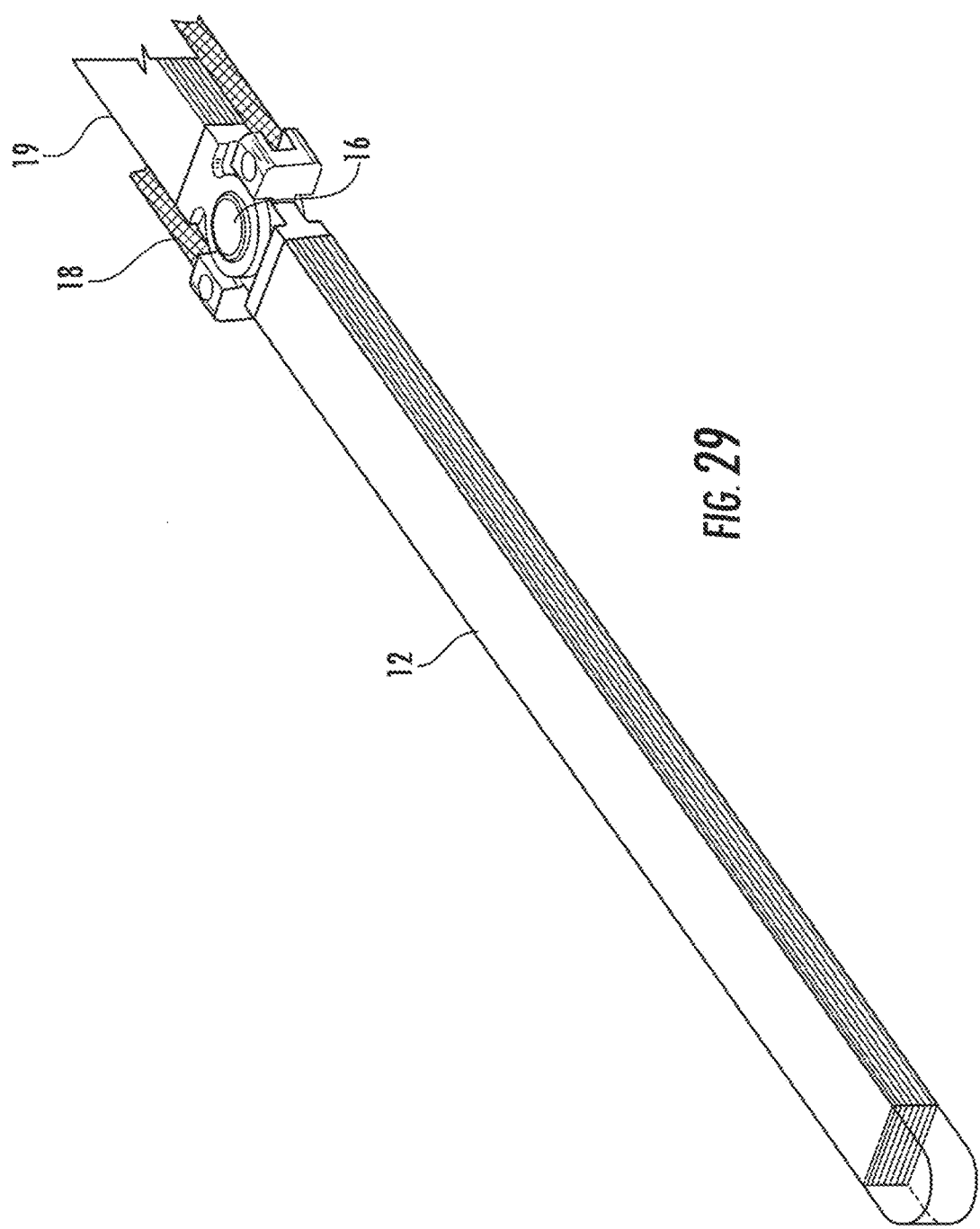
FIG. 29 is a perspective view of another example mechanical esophageal displacement system in accordance with the present disclosure.

FIG. 29 is a perspective view of another example mechanical esophageal displacement system in accordance with the present disclosure. Similar to the embodiment found in FIG. 1 above, the example mechanical esophageal displacement system of FIG. 29 includes pulleys and cables to articulate the respective segments of the esophageal positioning device.

Figure 30:
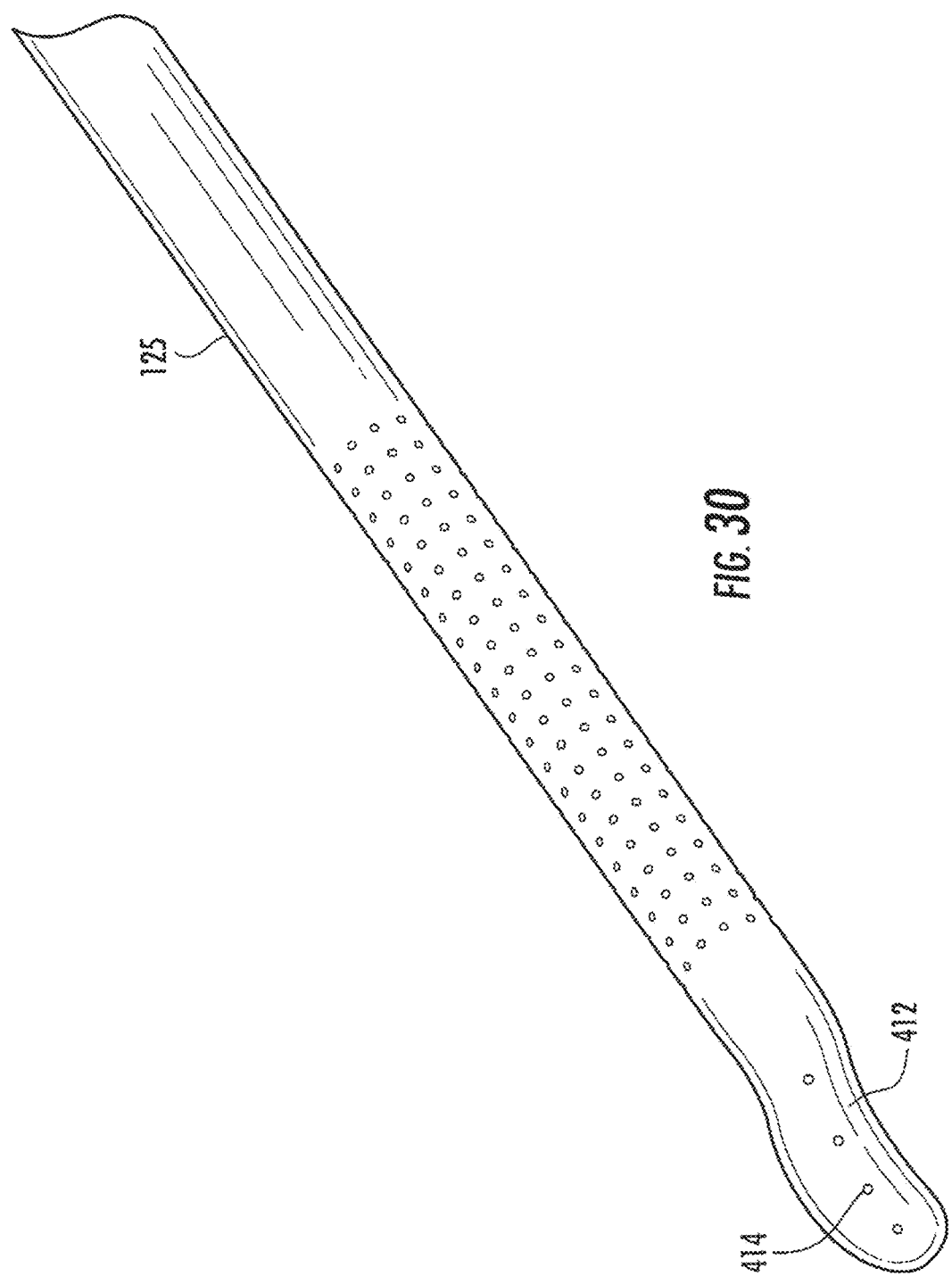
FIG. 30 is a perspective view of an example assembly of the mechanical esophageal displacement system of FIG. 29.

FIG. 30 is a perspective view of an example assembly of the mechanical esophageal displacement system of FIG. 29. The view shows an outer tube 125 having a long tail 412 with radiopaque markers 414.

Figure 31:
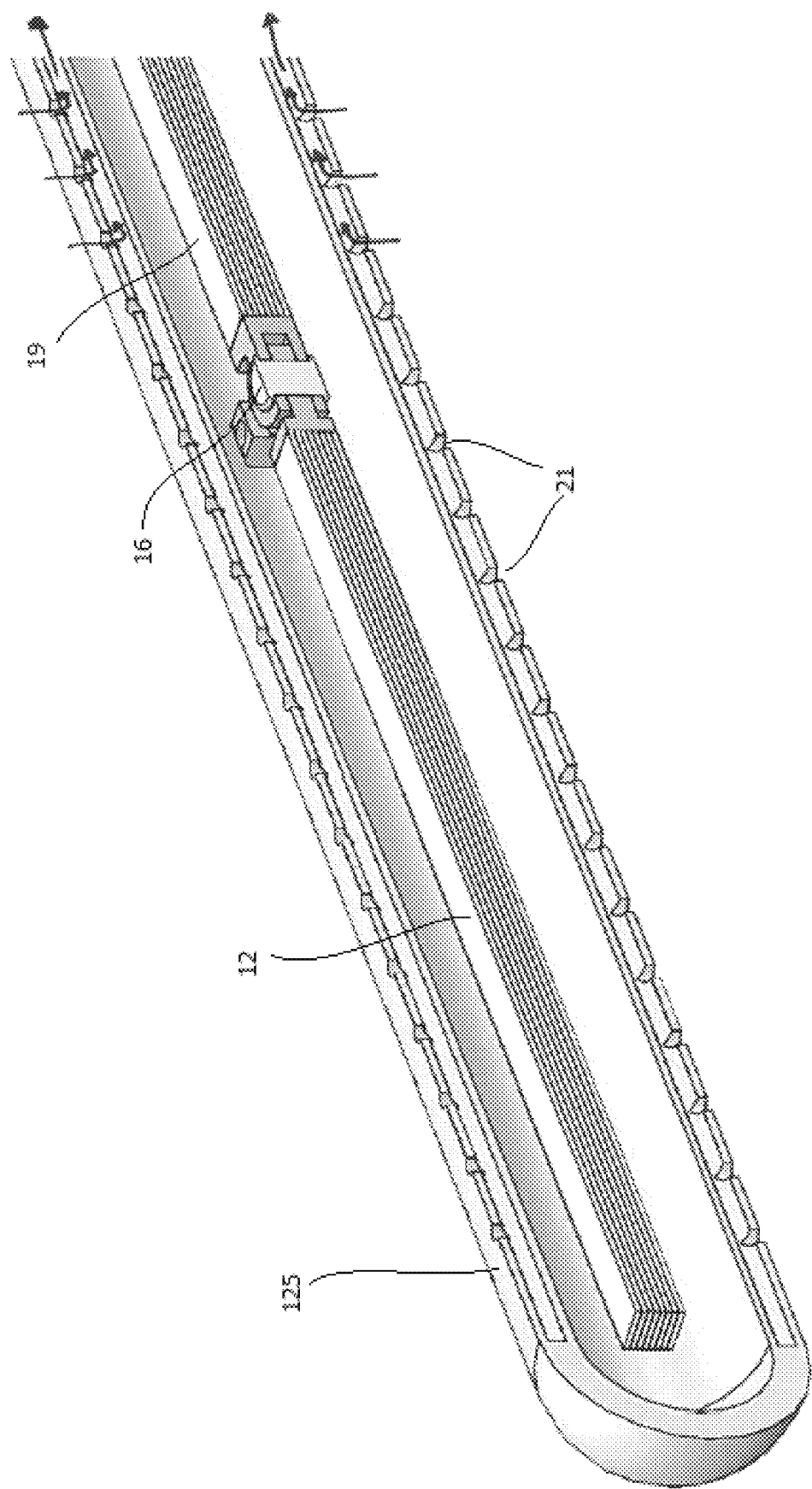
FIG. 31 is perceptive, cross sectional view of a portion of portion of the mechanical esophageal displacement system of FIG. 29.

FIG. 31 is perceptive, cross sectional view of a portion of the mechanical esophageal displacement system of FIG. 29. The view highlights vacuum passages 21 and holes of the assembly.

Figure 32:
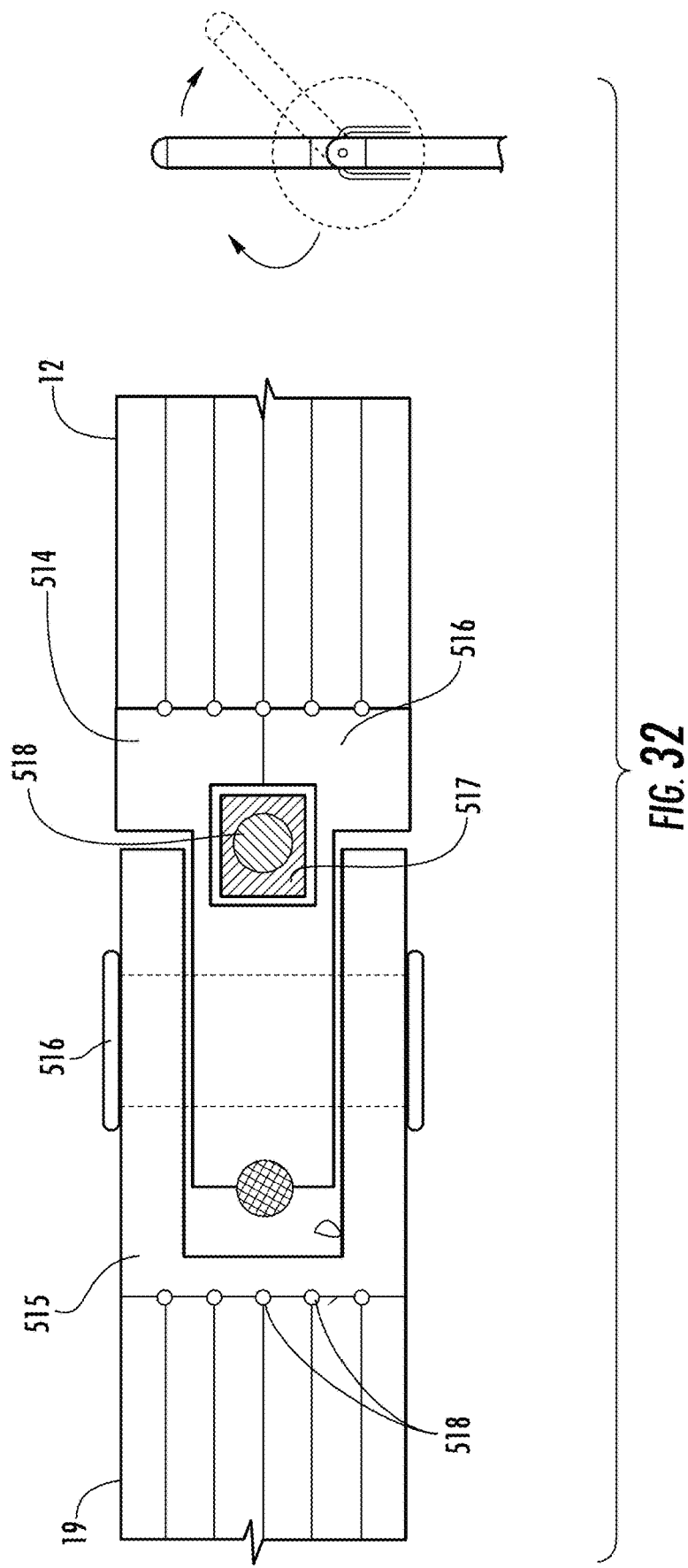
FIG. 32 is a front view of a portion of portion of the mechanical esophageal displacement system of FIG. 29.

FIG. 32 is a front view of a portion of the mechanical esophageal displacement system of FIG. 29. The view highlights the connection between the segments of the esophageal positioning device. The view includes a clevis 515, pin 516, cable 518, crimp 517, welds 518, and top 514 and bottom 516 pulley halves.

Figure 33:
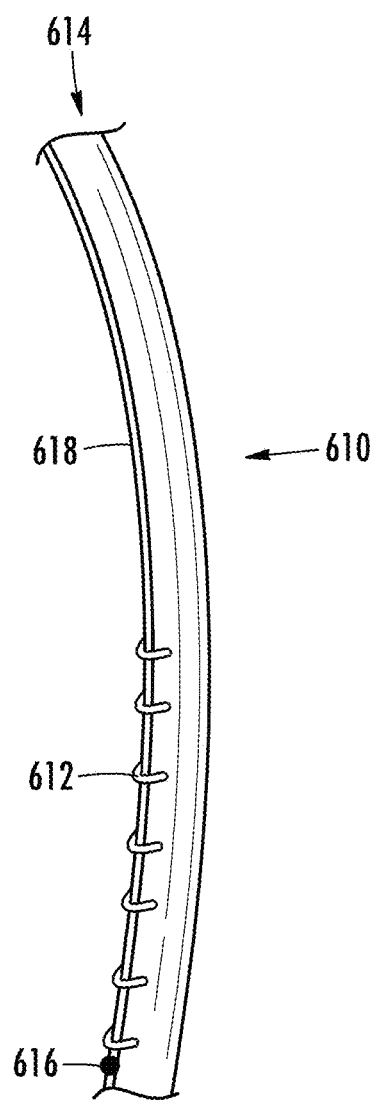
FIG. 33 is a perceptive view of another example mechanical esophageal displacement system in accordance with the present disclosure.

FIG. 33 is a perceptive view of another example mechanical esophageal displacement system in accordance with the present disclosure. The view shows an esophageal positioning device having a fishing rod 610, eyelets 612, a cinch wire 614, and cables 618, in which the cables house an anchor 616.

Figure 34:
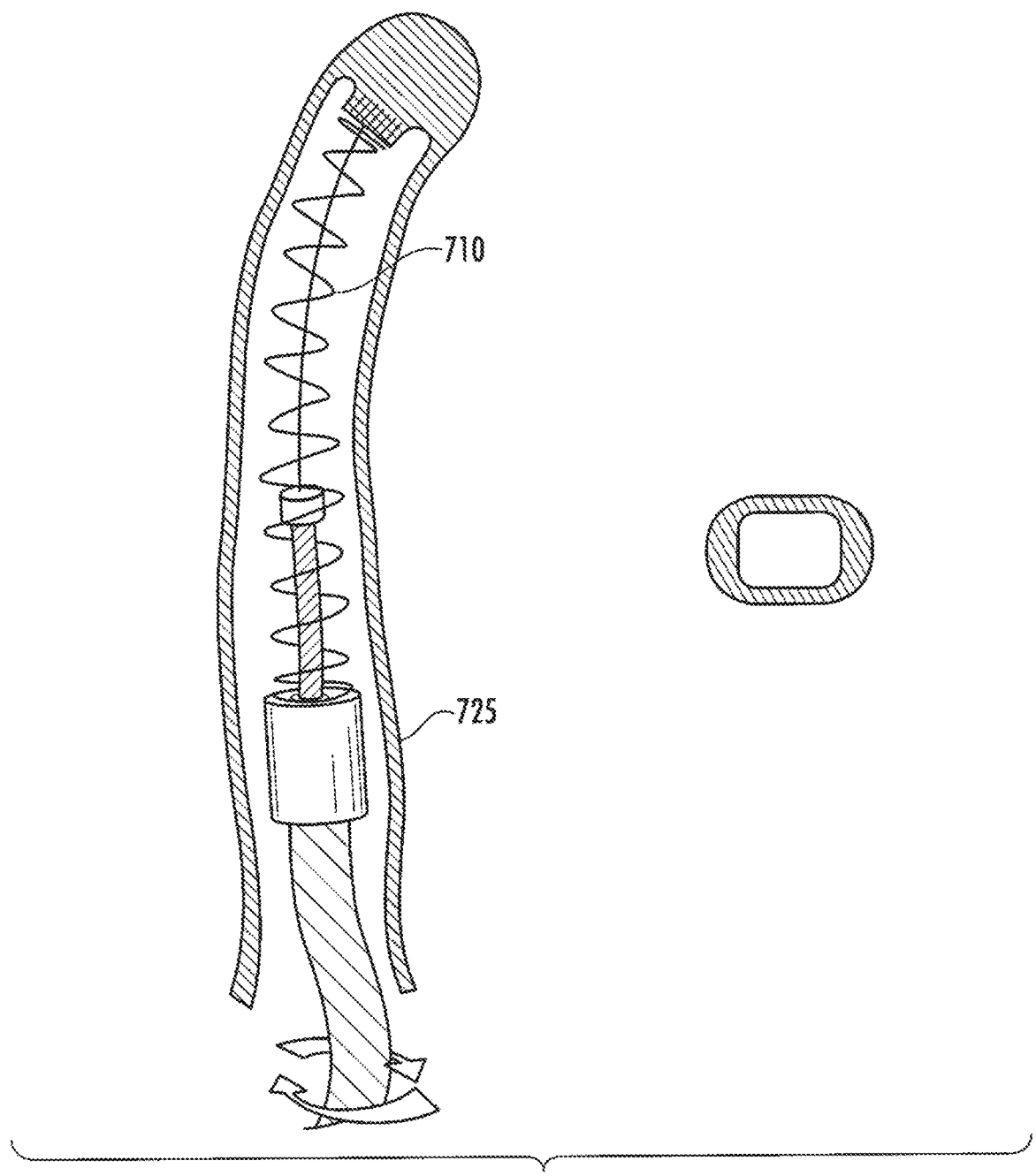
FIG. 34 is a perceptive, cross sectional view of another example mechanical esophageal displacement system in accordance with the present disclosure.

FIG. 34 is a perceptive, cross sectional view of another example mechanical esophageal displacement system in accordance with the present disclosure. The mechanical esophageal displacement system of FIG. 34 includes an esophageal displacement device that rotates to compress a spring 710 operatively coupled to the assembly.

Figure 35:
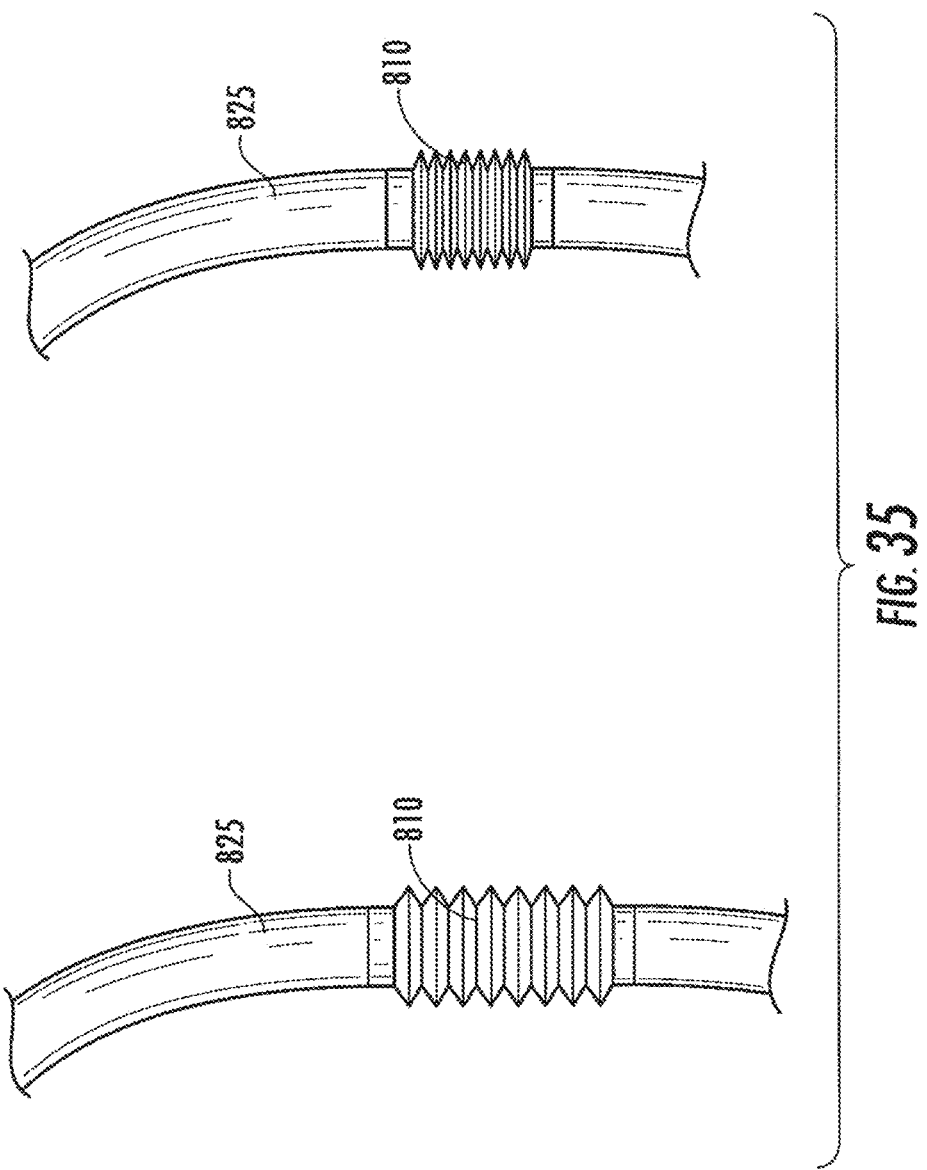
FIG. 35 is a perspective view of another example assembly in accordance with the present disclosure.

FIG. 35 is a perspective view of another example assembly in accordance with the present disclosure. In FIG. 35, the assembly includes a tube 825 having a collapsible portion 810, in which the collapsible portion 810 can be actuated by guide wires and/or vacuum pressure.

Figure 36:
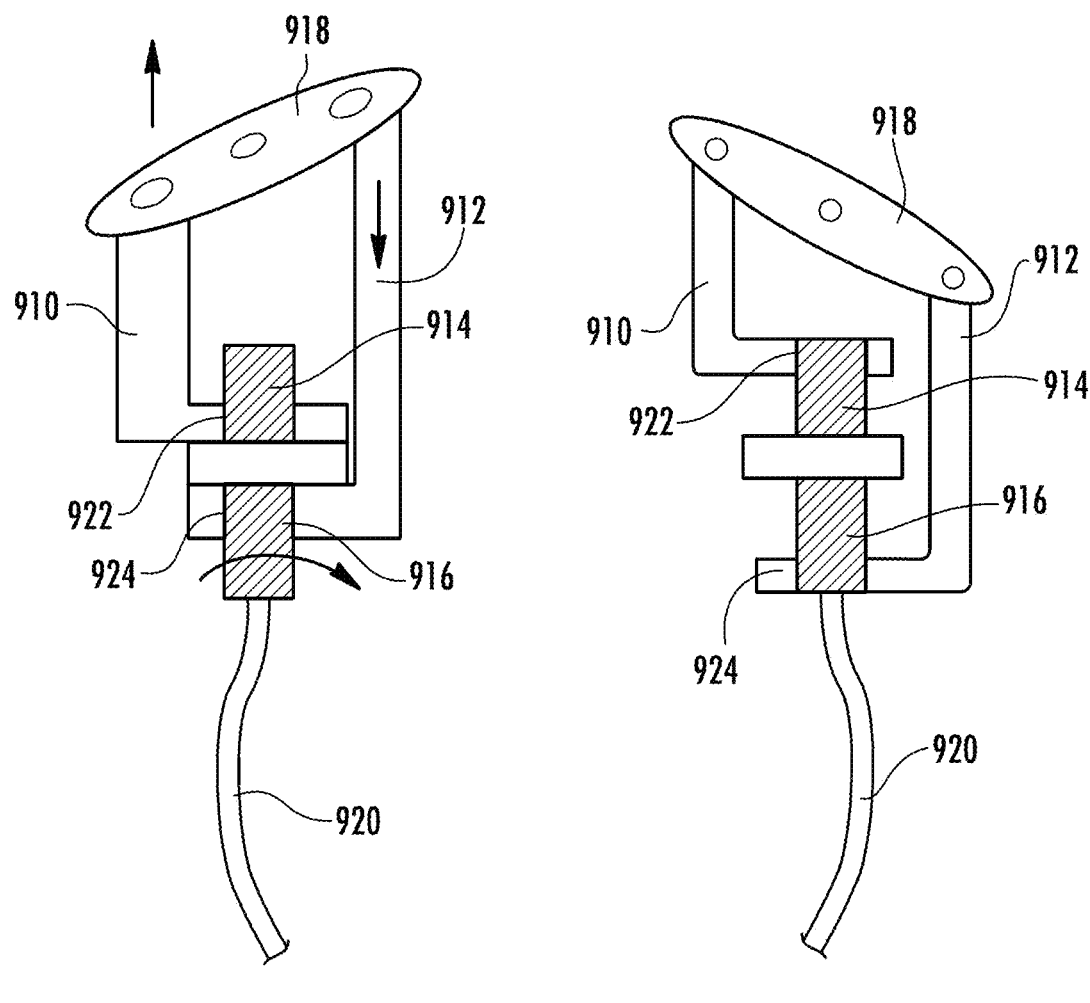
FIG. 36 is a perspective view of another example mechanical esophageal displacement system in accordance with the present disclosure.

FIG. 36 is a perspective view of another example mechanical esophageal displacement system in accordance with the present disclosure. The mechanical esophageal displacement system of FIG. 36 includes an esophageal displacement device that provides articulation via shafts 910, 912, a right-hand threaded rod 914, and a left-hand threaded rod 916, wherein the right-hand threaded rod 914 and a left-hand threaded rod 916 are coupled together axially. When a cable 920 connected to the left-hand threaded rod is rotated, threaded openings 922, 924 in shafts 910, 912, respectively, are moved up and down the threaded rods 914, 916, tilting an articulation plate 918 hingedly connected to the opposite ends of the shafts 910, 912.

Figure 37:
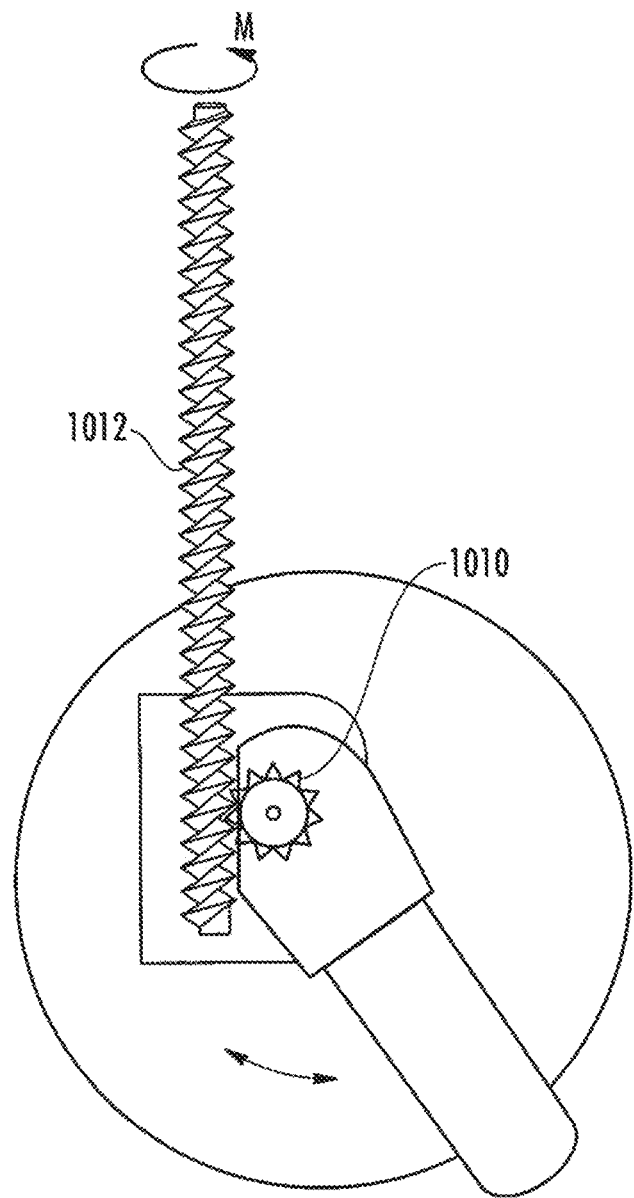
FIG. 37 is a perspective view of another example mechanical esophageal displacement system in accordance with the present disclosure.

FIG. 37 is a perspective view of another example mechanical esophageal displacement system in accordance with the present disclosure. The mechanical esophageal displacement system of FIG. 37 includes a gear drive 1010 that provides articulation via a worm gear 1012.

Figure 38:
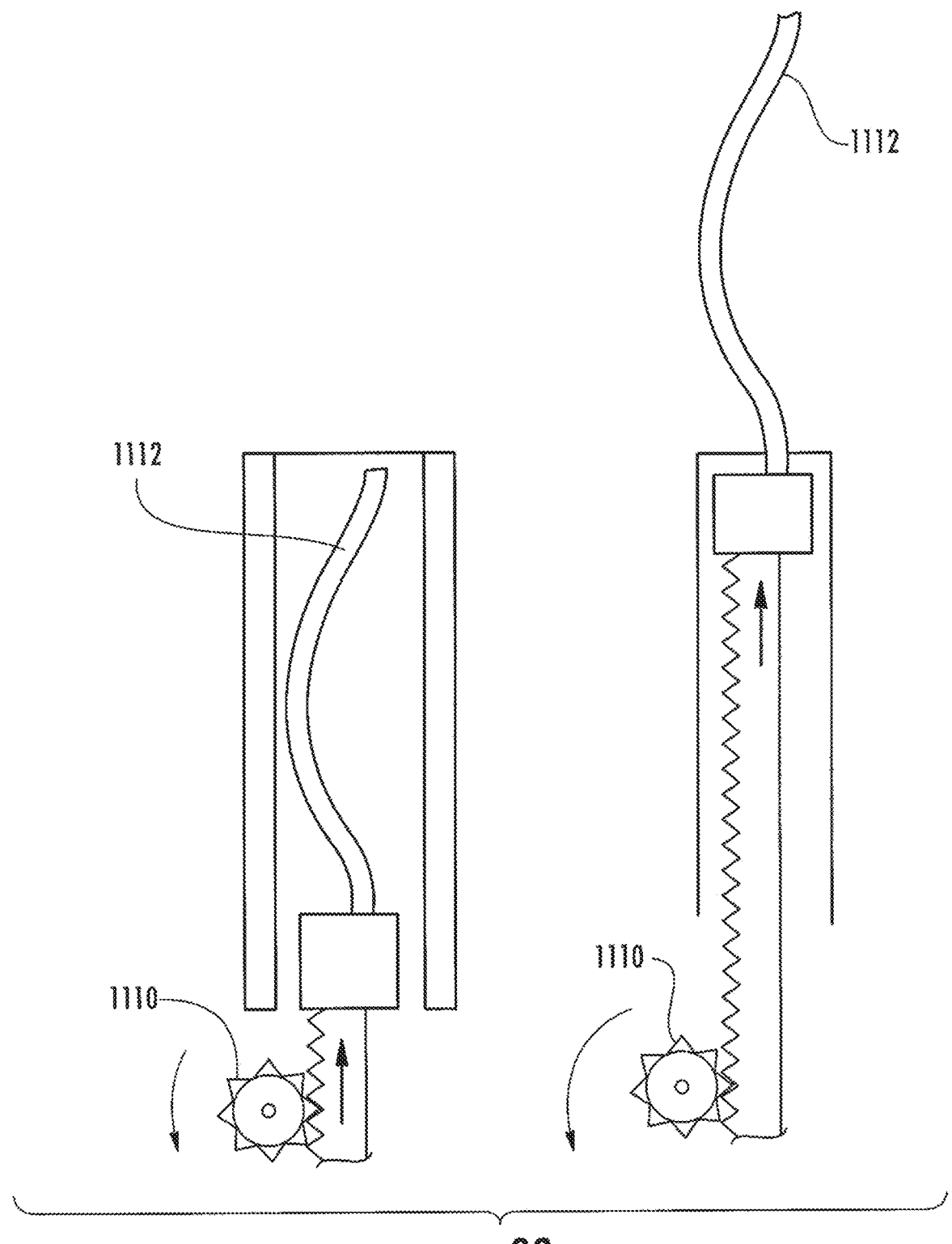
FIG. 38 is a perspective view of another example mechanical esophageal displacement system in accordance with the present disclosure.

FIG. 38 is a perspective view of another example mechanical esophageal displacement system in accordance with the present disclosure. The mechanical esophageal displacement system of FIG. 38 includes a gear drive 1110 that provides articulation via a leaf spring 1112.

Figure 39:
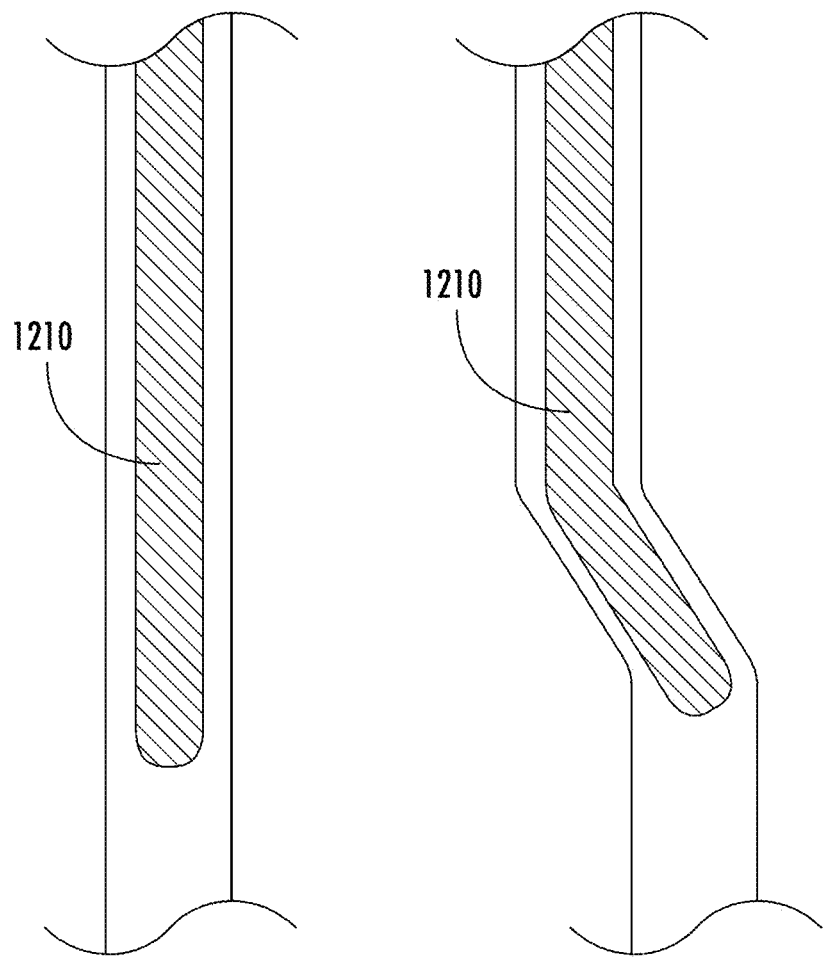
FIG. 39 is a perspective view of another example assembly in accordance with the present disclosure.

FIG. 39 is a perspective view of another example assembly in accordance with the present disclosure. In FIG. 39, the assembly includes an outer tube 1210, similar to outer tube 125, made of a material that deforms to a particular shape when wet.

Figure 40:
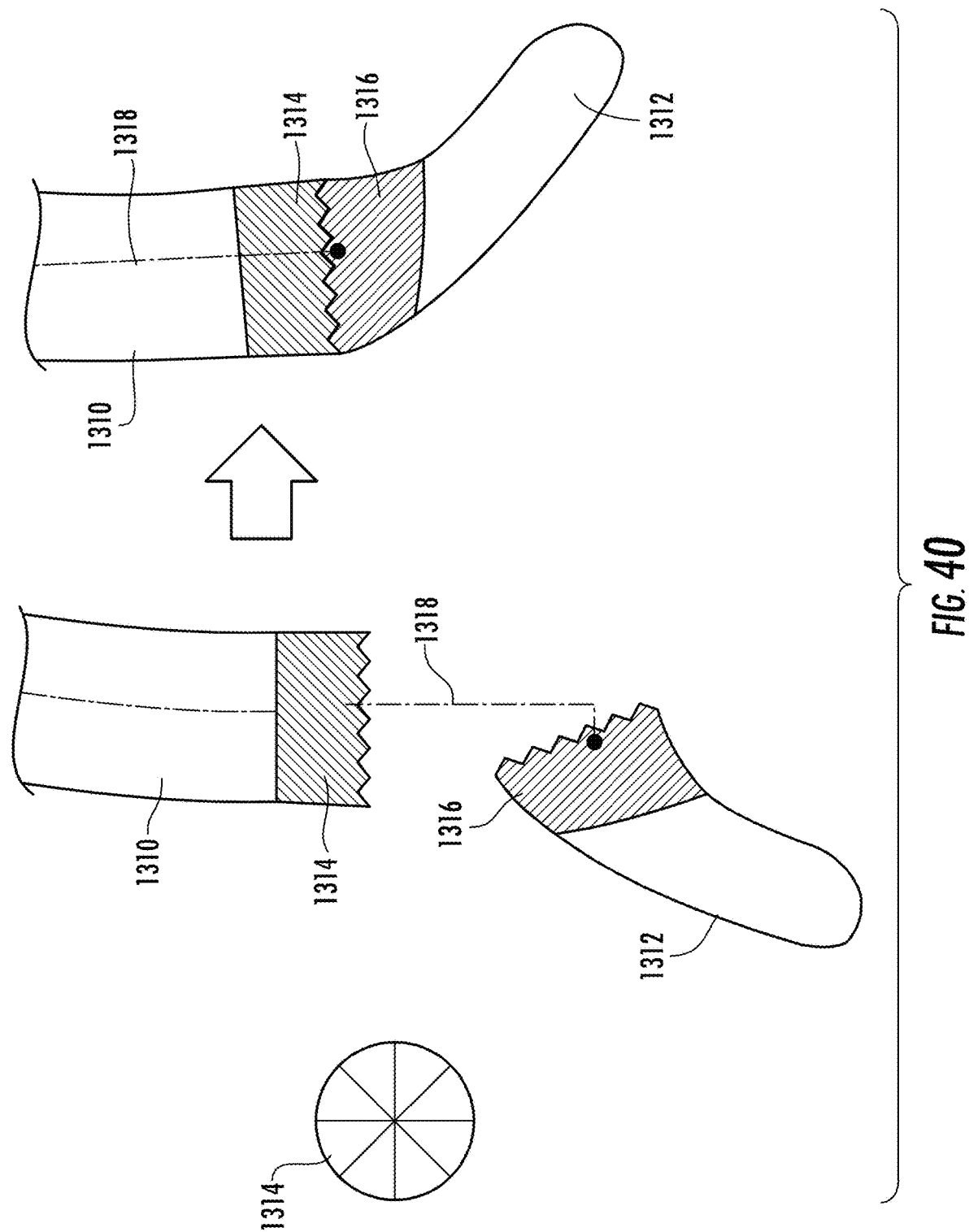
FIG. 40 is a perspective view of another example mechanical esophageal displacement system in accordance with the present disclosure.

FIG. 40 is a perspective view of another example mechanical esophageal displacement system in accordance with the present disclosure. The mechanical esophageal displacement system of FIG. 40 includes a top 1310 and bottom section 1312 that are matched together via a set of axial ridges 1314, 1316, respectively, in which the axial ridges 1314, 1316 prevent rotation. The top 1310 and bottom sections 1312 are connected loosely via a wire 1318. The bottom section 1312 is locked into place when the wire 1318 is pulled up.

Figure 41:
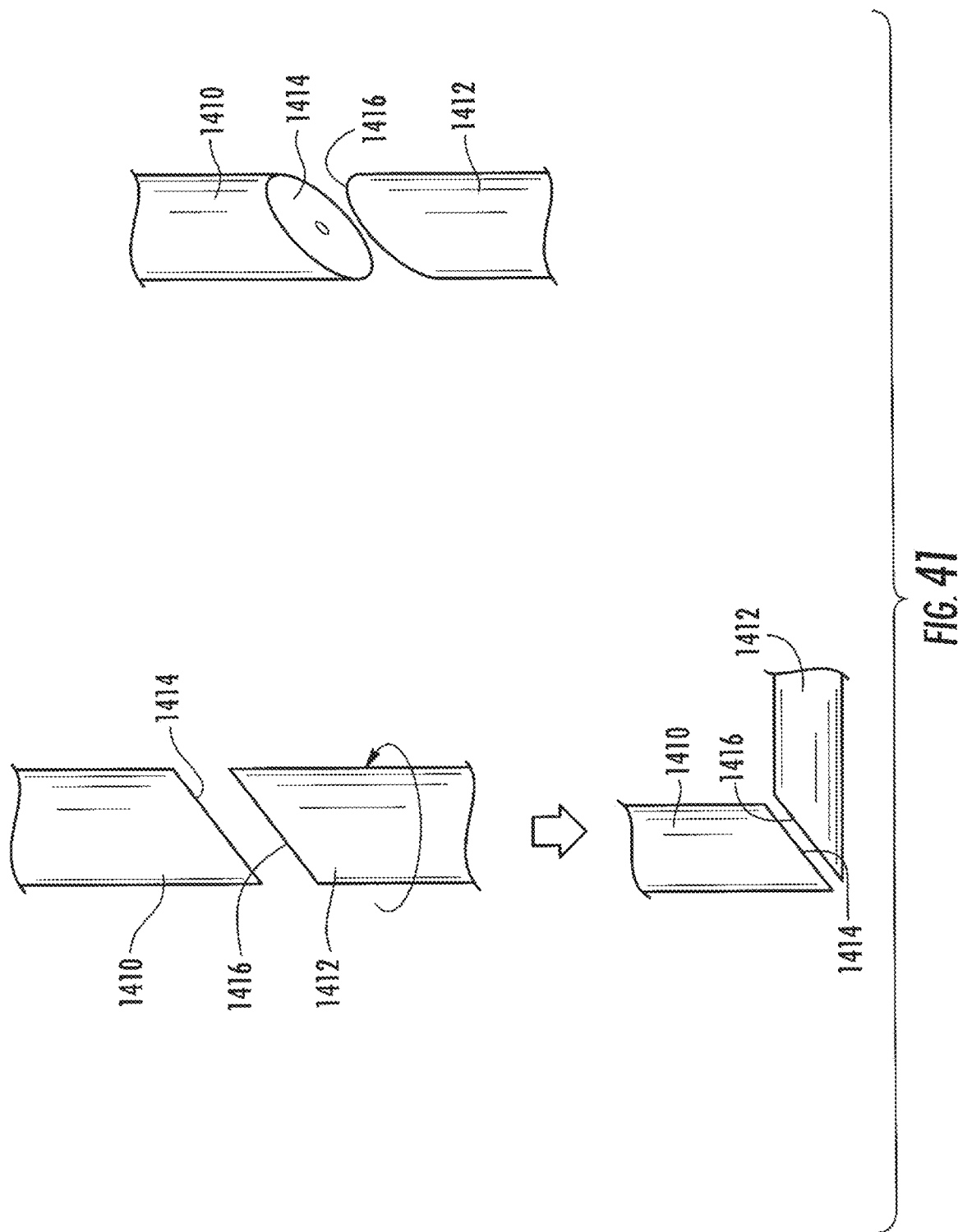
FIG. 41 is a perspective view of another example mechanical esophageal displacement system in accordance with the present disclosure.

FIG. 41 is a perspective view of another example mechanical esophageal displacement system in accordance with the present disclosure. The mechanical esophageal displacement system of FIG. 40 includes an esophageal displacement device having two pieces 1410, 1412 having angled faces 1414, 1416, respectively, in which the angle between of the two pieces 1410, 1412, changes from being aligned to being perpendicular upon rotation.

Figure 42:
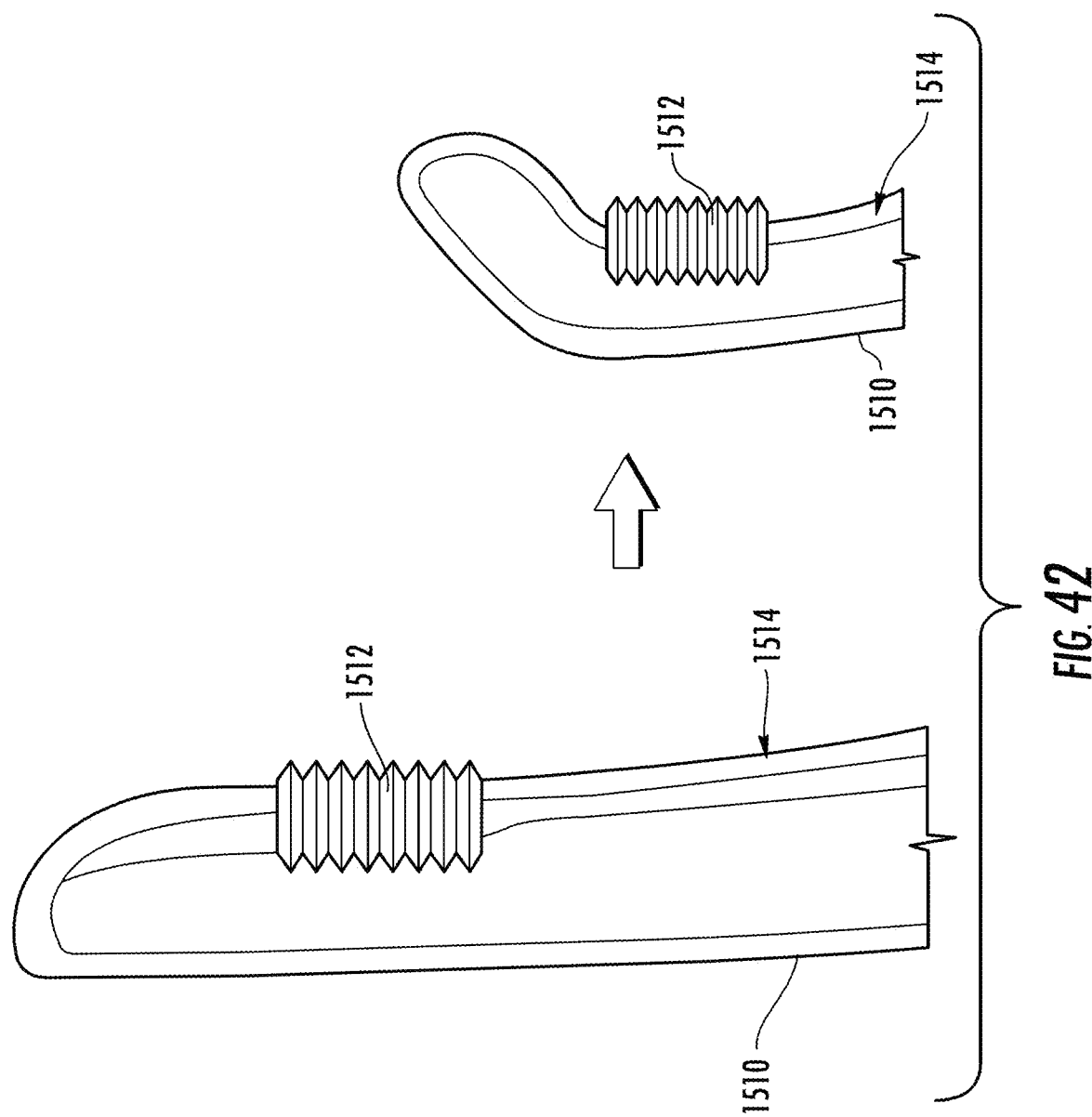
FIG. 42 is a perspective view of another example assembly in accordance with the present disclosure.

FIG. 42 is a perspective view of another example assembly in accordance with the present disclosure. The assembly of FIG. 42 includes a straw like tube 1510 that has a flexible portion 1512 only on one side 1514, thus the vacuum when applied causes the one side 1514 of the assembly to deflect.

Figure 43:
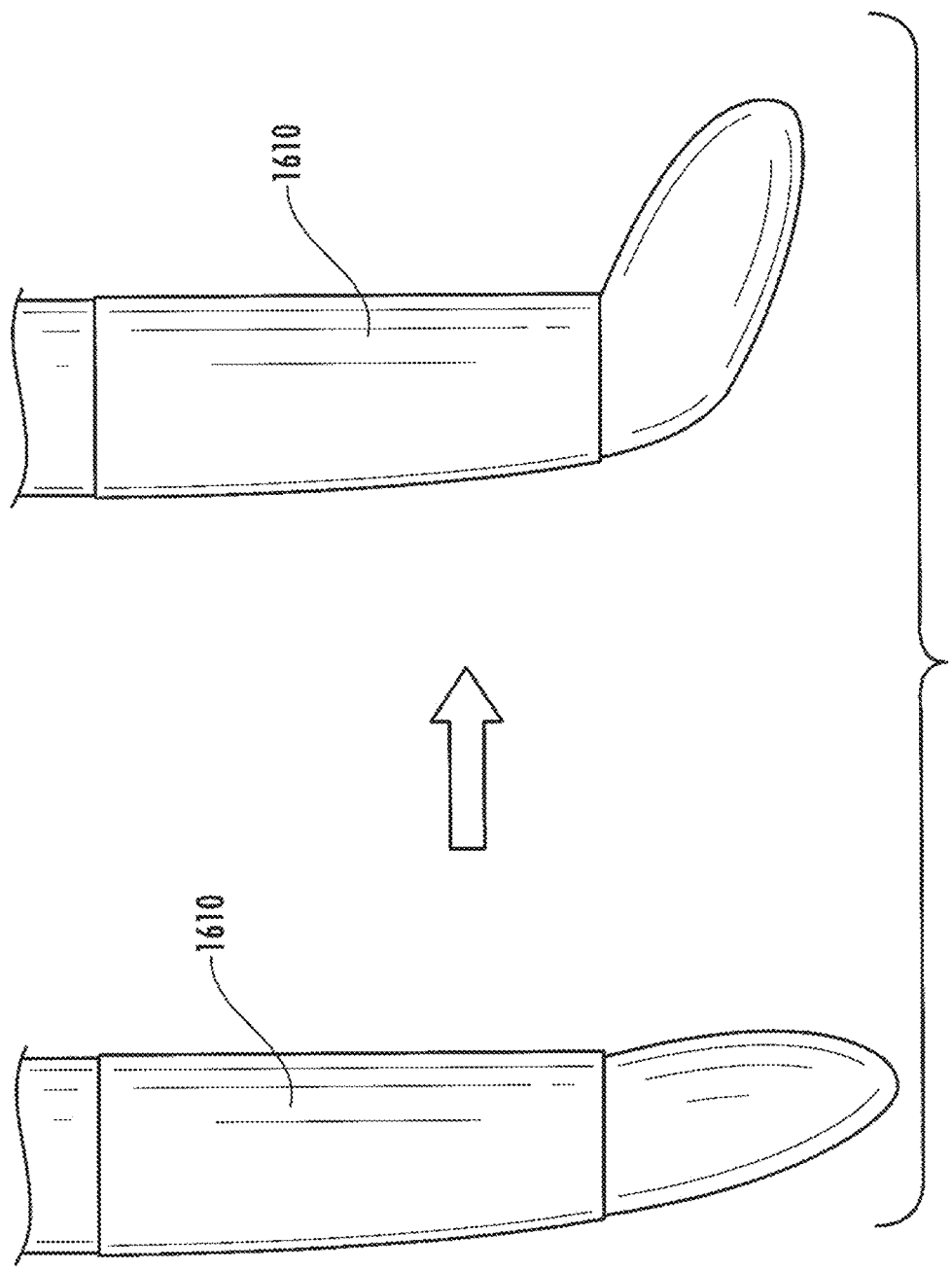
FIG. 43 is a perspective view of another example assembly in accordance with the present disclosure.

FIG. 43 is a perspective view of another example assembly in accordance with the present disclosure. The assembly of FIG. 43 includes a gel liquid portion 1610 that causes the assembly to deflect in a given direction.

Figure 44:
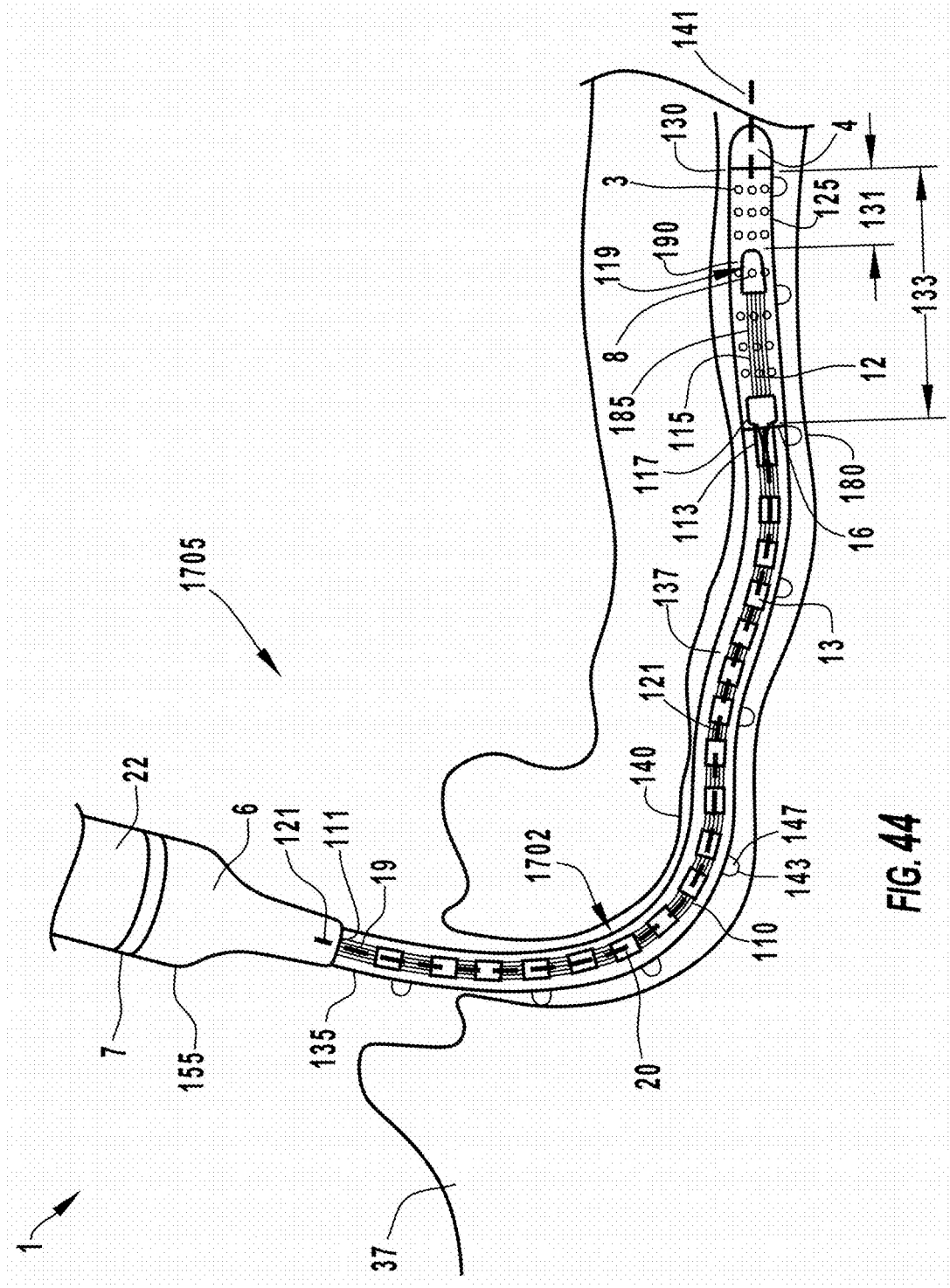
FIG. 44 is a side view of a mechanical esophageal displacement, according to another implementation.

FIG. 44 shows an assembly 1705 for use with a vacuum system (not shown) and an esophageal positioning device 1713, according to another implementation. The assembly 1705 includes an introducer 1702 and a handle 105.

The assembly 1705 shown in FIG. 44 is similar to the assemblies in the embodiments shown in FIGS. 1-43. Thus, similar reference numbers to those used for the assemblies shown in FIGS. 1-43 are used to indicate similar features included in the assembly 1705 shown in FIG. 44. The esophageal positioning device 13 of assembly 1705 is the same as the esophageal positioning device 13 shown in FIGS. 1-43. The esophageal positioning device 13 of assembly 1705 includes a first segment 110 and a second segment 115. The first segment 110 has a proximal end 111 coupled to the handle, a distal end 113 distal to and spaced apart from the proximal end 111, and a central axis 121 extending from the proximal end 111 to the distal end 113. The second segment 115 has a proximal end 117 pivotally connected to the distal end 113 of the first segment 110 by a pivot pin 16 and a distal end 119 distal to and spaced apart from the proximal end 117 of the second segment 115. In some implementations, the length of the second segment 115 as measured from the proximal end 117 to the distal end 119 is 40 mm or more.

The second segment 115 is pivotable about the pivot pin 16 between a first position and a second position. In the first position, the distal end 119 of the second segment 115 is disposed along the central axis 121 of the first segment 110, and in the second position, the distal end 119 of the second segment 115 is displaced from the central axis 121.

As with the esophageal positioning devices 13 shown in FIGS. 1-43, the first segment 110 of the esophageal positioning device 13 shown in FIG. 44 includes a proximal band assembly 19, and the second segment 115 includes a distal band assembly 12. The distal band assembly 12 includes a plurality of distal bands 185 in which the distal ends 190 of the bands 185 are slidable along the central axis 121 relative to each other.

The introducer 1702 includes a soft outer tube 125 sized to pass through a mouth or nasal passage into an esophagus. The outer tube 125 includes a proximal end 135, a distal end 130 distal to and spaced apart from the proximal end 135, a body 140 extending between the proximal end 135 and distal end 130, and a longitudinal axis 141 extending along the body 140 from the proximal end 135 to the distal end 130. The introducer 1702 also includes a tube tip 4 located at the distal end 130 of the outer tube 125. The introducer 1702 further includes a plurality of eyelets 143 extending radially outward from the outer tube 125. Each of the eyelets 143 shown in FIG. 44 defines an eyelet opening 147. The eyelet openings 147 of each of the one or more eyelets 143 are axially aligned with each other along the outer tube 125 such that a wire, cable, or tube can be disposed within each of the eyelet openings 147. The eyelets 143 couple the wire, cable, or tube to the outer tube 125 to provide communication with a device disposed on the assembly.

The outer tube 125 is sized such that the esophageal positioning device 13 is insertable into the introducer 1702. As shown in FIG. 44, when the esophageal positioning device 13 is disposed into the introducer 1702, a gap portion 131 of the body 140 of the outer tube 125 is defined along the longitudinal axis 141 between the tube tip 4 of the introducer 1702 and the distal end 119 of the second segment 115 of the esophageal positioning device 13. The body 140 of the outer tube 125 has an end portion 133 as measured along the longitudinal axis 141 from the tube tip 4 to the pivotal connection between the first segment 110 and the second segment 115 of the esophageal positioning device 13 when the esophageal positioning 13 device is disposed within the introducer 1702.

In the implementation shown in FIG. 44, the length of the gap portion 131 of the outer tube 125 as measured along the longitudinal axis 141 is 28 mm. However, in other implementations, the length of the gap portion of the outer tube as measured along the longitudinal axis is from 25 mm to 30 mm. In some implementations, the length of the gap portion of the outer tube as measured along the longitudinal axis is from 10 mm to 30 mm.

The body 140 defines a plurality of radial vacuum holes 3 spaced circumferentially around the longitudinal axis 141. The plurality of radial vacuum holes 3 is in fluid communication with the vacuum system to apply a vacuum to an esophageal wall. Only the end portion 133 of the body 140 of the outer tube 125 defines the plurality of radial vacuum holes 3. The radial vacuum holes 3 in the body 140 of the outer tube 125 shown in FIG. 44 are arranged in eight rings of eight circumferentially spaced vacuum holes 3. However, in other implementations, the rings of circumferentially spaced vacuum holes include any number of circumferentially spaced vacuum holes. In some implementations, the rings of circumferentially spaced vacuum holes include any number of circumferentially spaced vacuum holes. In some implementations, the different rings of circumferentially spaced vacuum holes include different numbers of circumferentially spaced vacuum holes. In some implementations, the plurality of vacuum holes are not arranged in rings and are arranged in any pattern.

The gap portion 131 of the outer tube 125 shown in FIG. 44 defines three of the eight rings of circumferentially spaced vacuum holes 3. As seen in FIG. 44, the distances, as measured along the longitudinal axis 141, between adjacent rings of circumferentially spaced vacuum holes 3 vary along the outer tube 125. The distances between adjacent rings of circumferentially spaced vacuum holes 3 defined by the gap portion 131 are the shortest distances between adjacent rings of vacuum holes 3 defined by the body 140 of the outer tube 125. Thus, the gap portion 131 defines the highest density of radial vacuum holes 3 of any portion of the body 140 of the outer tube 125 of the introducer 1702.

In use, the introducer 1702 of the assembly 1705 is inserted into the nose or mouth of a patient and advanced into the esophagus, and the esophageal positioning device 13 is advanced through the outer tube 125 of the introducer 1702. In some implementations, after the introducer 1702 and esophageal positioning device 13 are advanced to a desired location in the esophagus, a contrast fluid is introduced through the introducer 1702 such that the contrast fluid flows through the vacuum holes 3. The contrast fluid can be detected by X-ray or fluoroscopy to determine the position of the assembly 1705 in the esophagus. Once the introducer 1702 and esophageal positioning device 13 are in the desired position in the esophagus of the patient, the vacuum system is engaged. The vacuum system creates a suction force in the vacuum holes 3 of the introducer 1702, causing a portion of the outer tube 125 to adhere to the esophageal wall. The second segment 115 of the esophageal positioning device 13 is then articulated about the first segment 110 from an initial position to a second position such that a portion of the esophagus is displaced a desired distance. Because the esophageal wall is adhered to the introducer 1702, the entire esophagus is able to be moved.

The spacing and location of the vacuum holes 3 defined by the introducer 1702 increase the ability of the vacuum holes 3 to adhere to and gather the esophageal wall. Because the vacuum holes 3 are spaced circumferentially around the introducer 1702, the vacuum holes 3 are able to adhere to the entire circumferential area of a portion of the esophageal wall. This pulls in and gathers the esophageal wall against the introducer 1702 to ensure that the entire portion of the esophagus is being displaced upon articulation of the second segment 115 without dragging an unadhered tailing edge of the esophagus behind it.

During articulation of the second segment 115, the distal end 119 of the second segment 115 is the portion of the esophageal positioning device 13 that is displaced the furthest and is subject to the highest amount of torque. Thus, it is important that the esophagus be tightly adhered to the introducer 1702 adjacent the distal end 119 of the second segment 115 to provide optimal grip. The gap portion 131 of the introducer 1702 shown in FIG. 44 is designed to include the highest density of vacuum holes 3 along the introducer 1702. When the esophageal positioning device 13 is inserted into the introducer 1702, the second segment 115 of the esophageal positioning device 13 does not extend into the gap portion 131 of the introducer 1702. When suction is applied to the introducer 1702, the suction causes the introducer 1702 to collapse. The portions of the introducer 1702 that contain the esophageal positioning device 13 are limited in how far these portions can collapse by the size of the bands in the esophageal positioning device 13. However, the gap portion 131 is able to radially collapse further than the portions of the introducer 1702 that contain the esophageal positioning device 13. Because the gap portion 131 defines the highest density of vacuum holes 3, the esophageal wall can be gathered more tightly and into a smaller area by the vacuum holes 3 defined by the gap portion 131 of the introducer 1702. The collapsibility of the gap portion 131 of the introducer 1702 and the high density of vacuum holes 3 defined by the gap portion 131 of the introducer 1702 ensure that the esophagus is adhered to the end of the introducer 1702 tightly.

The higher density of vacuum holes 3 defined by the gap portion 131 also allows a greater amount of contrast fluid to flow through the gap portion 131 of the introducer 1702. When viewed through X-ray or fluoroscopy, the greater amount of contrast fluid entering into the portion of the esophagus in the vicinity of the gap portion 131 allows the end of the introducer 1702, where the gap portion 131 is located, to be more easily detected.

Figure 45:
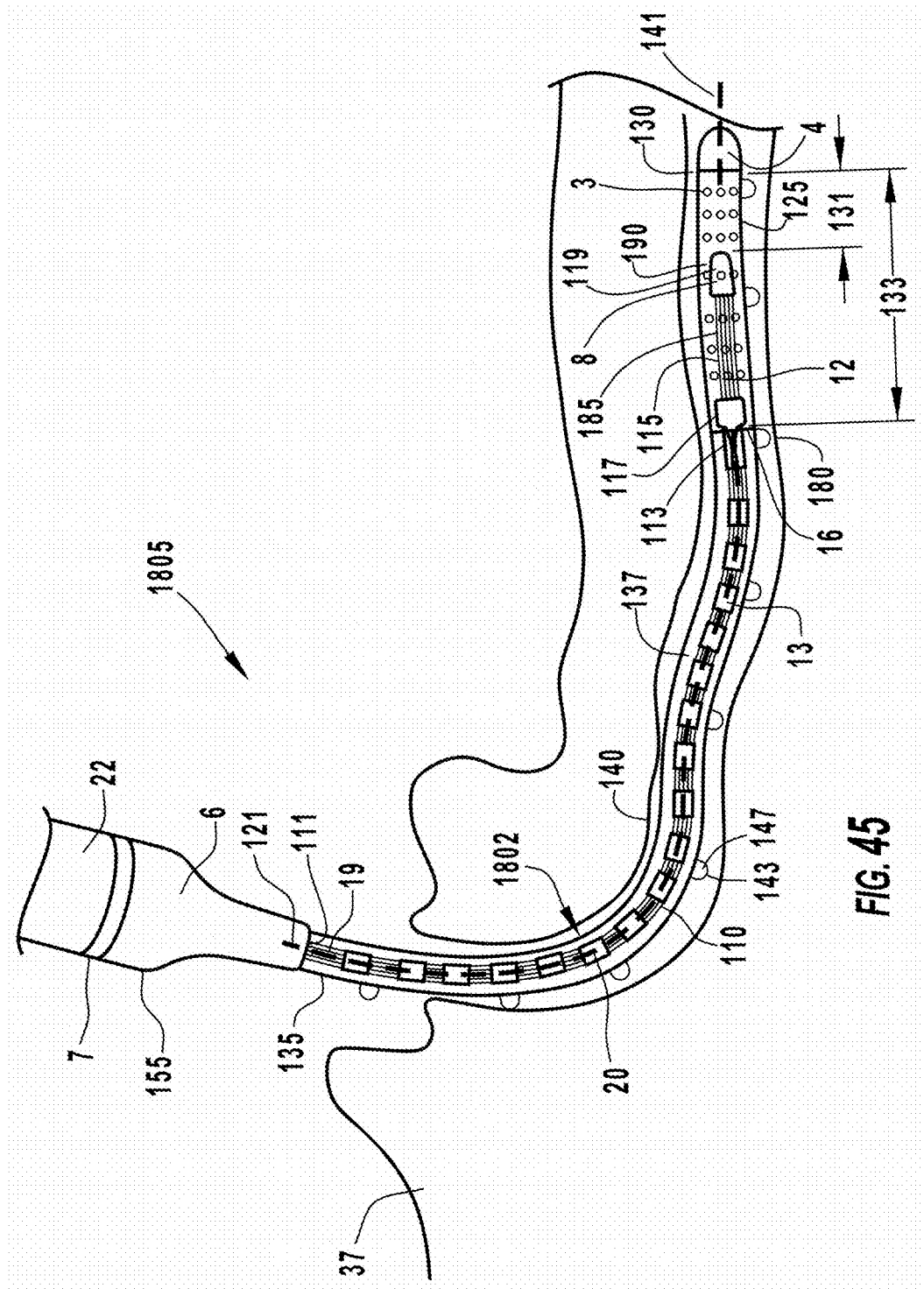
FIG. 45 is a side view of a mechanical esophageal displacement, according to another implementation.

FIG. 45 shows another implementation of an assembly 1805 including an introducer 1802. The assembly shown in FIG. 45 is similar to the assembly 1705 in the embodiment shown in FIG. 44. Thus, similar reference numbers to those used for the assembly 1705 shown in FIG. 44 are used to indicate similar features included in the assembly 1805 shown in FIG. 45. The gap portion 131 of the introducer 1802 shown in FIG. 45 defines a density of radial vacuum holes 3 that is highest adjacent the distal end 130 of the outer tube 125. The density of radial vacuum holes 3 gradually decreases along the longitudinal axis 141 in a direction from the distal end 130 of the outer tube 125 toward the proximal end 135 of the outer tube 125.

Figure 46:
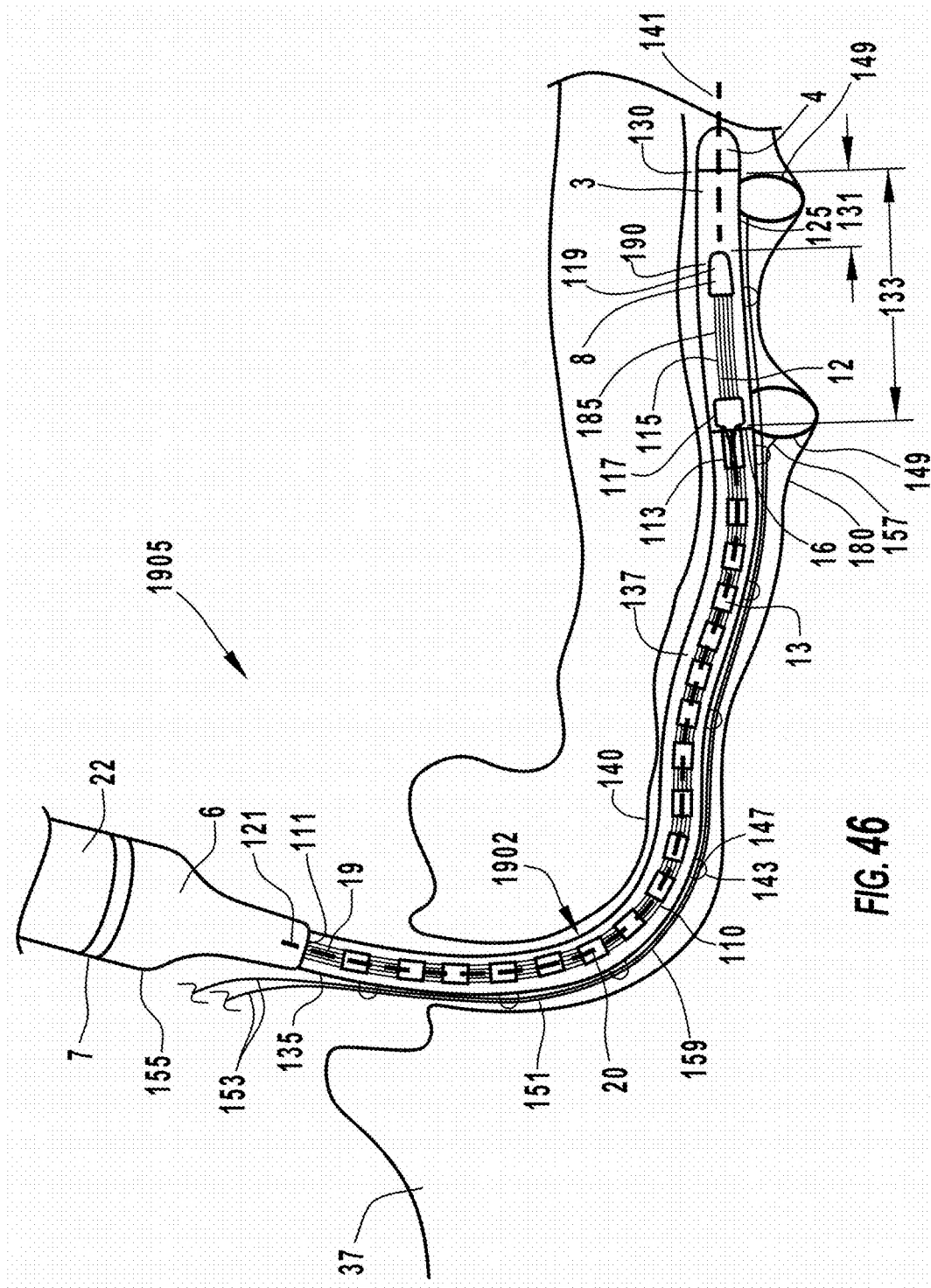
FIG. 46 is a side view of a mechanical esophageal displacement, according to another implementation.

FIG. 46 shows another implementation of an assembly 1905 including an introducer 1902. The assembly 1905 shown in FIG. 46 is similar to the assemblies 1705, 1805 in the embodiments shown in FIGS. 44-45. Thus, similar reference numbers to those used for the assemblies 1705, 1805 shown in FIGS. 44-45 are used to indicate similar features included in the assembly 1905 shown in FIG. 46. However, the introducer 1902 shown in FIG. 46 includes two occlusion balloons 149: a proximal balloon and a distal balloon. The occlusion balloons 149 are disposed on the outer surface of the body 140 of the outer tube 125 and are extendable radially outwardly from the outer tube 125. The proximal balloon 149 is disposed adjacent a proximal end of the end portion 133 of the outer tube 125 located at the pivotal connection between the first segment 110 and the second segment 115 of the esophageal positioning device 13 when the esophageal positioning device 13 is disposed within the introducer 1902. The distal balloon 149 is disposed adjacent a distal end of the end portion 133 of the outer tube 125. Thus, all of the vacuum holes 3 are defined between the proximal balloon 149 and the distal balloon 149.

The assembly also includes two inflation tubes 151. Each inflation tube 151 has a first end 153, a second end 157 and spaced apart from the first end 153 of the inflation tube 151, and body 159 extending from the first end 153 of the inflation tube 151 to the second end 157 of the inflation tube 151. Each of the occlusion balloons 149 are coupled to the second end 157 of one of the inflation tubes 151. The bodies 159 of each of the inflation tubes 151 extends through the eyelet openings 147 of the eyelets 143 of the outer tube 125 such that the bodies 159 of the inflation tubes 151 are coupled to the body 140 of the outer tube 125. The inflation tubes 151 extend along the outer tube 125 such that the first ends 153 of the inflation tubes 151 are adjacent the proximal end 135 of the outer tube 125. The first ends 153 of the inflation tubes 151 are each coupled to a pump (not shown) for inflating the occlusion balloons 149. The pumps can be manual pumps or automatic pumps.

When the introducer 1702 and esophageal positioning device 13 are disposed in the esophagus of a patient, the pumps are activated to cause air to flow from the pump, through the inflation tubes 151, and into the occlusion balloons 149. The occlusion balloons 149 are inflated such that the outer surface of the occlusion balloons 149 abut the inner wall of the esophagus and create a seal. Because all of the vacuum holes 3 are defined by the end portion 133 of the outer tube 125 between the proximal balloon 149 and the distal balloon 149, the only portion of the esophagus that is introduced to suction by the vacuum holes 3 is the portion occluded by the occlusion balloons 149.

While some of the means for deflecting the assembly have been described above, it should be noted that the assembly can also be articulated using any other mean known in the art, including, for example, spring, fluid/air-filled container, magnets, etc.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present invention.

Disclosed are materials, systems, devices, compositions, and components that can be used for, can be used in conjunction with, can be used in preparation for, or are products of the disclosed methods, systems and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein.

What is claimed is:

1. A mechanical esophageal displacement system comprising:
  an assembly that is to be operatively coupled to a vacuum system, the assembly comprising:
    an introducer sized to receive an esophageal positioning device, the introducer comprising:
      a soft outer tube sized to pass through a mouth or nasal passage into an esophagus, the soft outer tube comprising a longitudinal axis, a distal end, a proximal end, and a body, wherein the body defines a plurality of radial vacuum holes spaced circumferentially around the longitudinal axis, wherein the plurality of vacuum holes are in fluid communication with the vacuum system to apply a vacuum to an esophageal wall; and
a tube tip located at the distal end of the outer tube; and the esophageal positioning device, wherein the esophageal positioning device includes:
a first segment; and
a second segment having a central axis, a proximal end pivotally connected to the first segment by a pivotal connection and a distal end opposite and spaced apart from the proximal end, the second segment being pivotable about the first segment between a first position and a second position upon articulation, wherein a gap portion of the soft outer tube is defined along the longitudinal axis between the tube tip of the introducer and the distal end of the second segment of the esophageal positioning device when the esophageal positioning device is disposed within the introducer, wherein the gap portion defines one or more of the plurality of radial vacuum holes, wherein the second segment comprises a distal band laminate assembly housing a plurality of distal bands in which distal ends of the plurality of distal bands are slidable along the central axis relative to each other.

2. The system of claim 1, wherein the gap portion defines a higher density of the plurality of radial vacuum holes than any other portion of the body of the outer tube.

3. The system of claim 1, wherein a density of the plurality of radial vacuum holes is highest adjacent the distal end of the soft outer tube, and the density of the plurality of radial vacuum holes gradually decreases along the longitudinal axis in a direction from the distal end of the soft outer tube toward the proximal end of the soft outer tube.

4. The system of claim 1, wherein the body of the soft outer tube has an end portion as measured along the longitudinal axis from the tube tip to the pivotal connection between the first segment and the second segment of the esophageal positioning device when the esophageal positioning device is disposed within the introducer, wherein only the end portion of the body of the soft outer tube defines the plurality of radial vacuum holes.

5. The system of claim 1, wherein a length of the gap portion of the soft outer tube as measured along the longitudinal axis is from 10 mm to 30 mm.

6. The system of claim 5, wherein the length of the gap portion of the soft outer tube as measured along the longitudinal axis is 28 mm.

7. The system of claim 5, wherein a length of the second segment is 40 mm or more.

8. The system of claim 1, wherein the introducer further comprises a plurality of eyelets extending radially outward from the soft outer tube, wherein each of the plurality of eyelets defines an eyelet opening and the eyelet openings of each of the plurality of eyelets are axially aligned with each other along the soft outer tube.

9. The system of claim 1, wherein the introducer further comprises one or more occlusion balloons extending radially outward from the soft outer tube, the one or more occlusion balloons being inflatable.

10. The system of claim 9, wherein the one or more occlusion balloons include a first occlusion balloon and a second occlusion balloon, the first occlusion balloon being disposed at the distal end of the soft outer tube and the second occlusion balloon being disposed at a portion of the soft outer tube that is adjacent the pivotal connection between the first segment and the second segment of the esophageal positioning device when the esophageal positioning device is disposed within the introducer.

* * * * *